US012782364B2

(12) United States Patent
El Balkhi et al.

(10) Patent No.: US 12,782,364 B2
(45) Date of Patent: Nov. 3, 2026

(54) METHODS AND KITS FOR DETECTING LIVER DYSFUNCTION IN A SUBJECT

(71) Applicants: INSERM (INSTITUT NATIONAL DE LA SANTÉ ET DE LA RECHERCHE MÉDICALE), Paris (FR); CENTRE HOSPITALIER REGIONAL UNIVERSITAIRE DE LIMOGES, Limoges (FR); UNIVERSITÉ DE LIMOGES, Limoges (FR)

(72) Inventors: Souleiman El Balkhi, Limoges (FR); Franck Saint Marcoux, Limoges (FR); Jean-Baptiste Woillard, Limoges (FR)

(73) Assignees: INSERM (INSTITUT NATIONAL DE LA SANTÉ ET DE LA RECHERCHE MÉDICALE), Paris (FR); CENTRE HOSPITALIER RÉGIONAL UNIVERSITAIRE DE LIMOGES, Limoges (FR); UNIVERSITÉ DE LIMOGES, Limoges (FR)

( * ) Notice: Subject to any disclaimer, the term of this patent is extended or adjusted under 35 U.S.C. 154(b) by 1172 days.

(21) Appl. No.: 17/295,584

(22) PCT Filed: Nov. 19, 2019

(86) PCT No.: PCT/EP2019/081801
§ 371 (c)(1),
(2) Date: May 20, 2021

(87) PCT Pub. No.: WO2020/104458
PCT Pub. Date: May 28, 2020

(65) Prior Publication Data

US 2022/0018852 A1 Jan. 20, 2022

(30) Foreign Application Priority Data

Nov. 20, 2018 (EP) .................................... 18306528

(51) Int. Cl.
*G01N 33/68* (2006.01)

(52) U.S. Cl.
CPC ... *G01N 33/6893* (2013.01); *G01N 2333/765* (2013.01); *G01N 2800/085* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 2003/0180820 A1* | 9/2003 | Bar-Or | G01N 33/68 | 435/7.32 |
| 2009/0280519 A1* | 11/2009 | Jalan | G01N 33/6893 | 436/88 |

FOREIGN PATENT DOCUMENTS

| | | | | |
|---|---|---|---|---|
| KR | 20130078628 | * | 7/2013 | G01N 21/17 |
| WO | WO-2007093902 A1 | * | 8/2007 | G01N 33/6803 |
| WO | 2013/024100 A2 | | 2/2013 | |
| WO | WO-2018193087 A1 | * | 10/2018 | G01N 33/538 |

OTHER PUBLICATIONS

Klammt et al: "Albumin-binding function is reduced in patients with decompensated cirrhosis and correlates inversely with severity of liver disease assessed by model for end-stage liver disease", European Journal of Gastroenterology and Hepatology, vol. 19(3): Mar. 2007, pp. 257-263 (IDS).*
Ge et al (Gastroenterology Research and Practice, 2016, 2016; article ID 5120760, 7 pages).*
Oettl et al (Journal of Hepatology, 2103, 59:978-983).*
Jalan et al (Hepatology, 2009, 50:555-564).*
Klammt et al (European Journal of Gastroenterology & Hepatology, 2007, 19:257-263) (IDS).*
Catalani et al (Hematology, 2011, Article ID 690620, 6 pages).*
Ordonez et al (Journal of Analytical Atomic Sepctriometry, 2009, 24:1037-1043).*
Kerger et al (Toxicology & Environmental Chemistry, 2013, 95:687-708).*
Lauwens et al (Talanta, Nov. 1, 2018, 189:332-338).*
Geib et al (Rapid Communications in Mass Spectrometry; Jun. 19, 2018; 32:1573-1582).*
Corrales Escobosa et al (Anal Bioanal Chem., 2015, 407:1149-1157).*
Klammt 2007 (European J of Gastroenterology & Hepatology, 2007, 19:257-263).*
Klammt 2008 (Liver Transplantation, 2008, 14:1333-1339).*
Kumar et al (Journal of Clinical and Diagnostic Research, 2016, 10:BC09-BC12).*
Eom et al (Analytical Sciences, 2014, 30:985-990).*
(Continued)

*Primary Examiner* — Laura B Goddard
(74) *Attorney, Agent, or Firm* — WCF IP

(57) ABSTRACT

Most chronic liver diseases are notoriously asymptomatic, until cirrhosis with clinical decompensation occurs. The use of early diagnosis strategies is vital to maintain patients in a symptom-free state and to delay decompensation, and thus improve the outcome. Albumin (HAS) undergoes several post-translational modifications in hepatocytes but clinical relevance of some of these modifications has been recently investigated in advanced liver diseases. Now, the inventors demonstrate that the binding capacities of some ligands, measured by inductively coupled plasma mass spectrometry (ICP-MS), are significantly different between cirrhotic patients and patients with no liver dysfunctions. The decreased binding capacities in cirrhotic patients were paralleled by the presence of significantly higher HSA isoforms Animal experimentations were also conducted to explore the precocity of HSA modifications in the course of chronic liver dysfunction. This allow the inventors to assume that the most important modifications of albumin structure due to liver dysfunction could be revealed by measuring the unbound fraction of specific ligands spiked in serum.

20 Claims, 14 Drawing Sheets

Figures 1A, 1B:
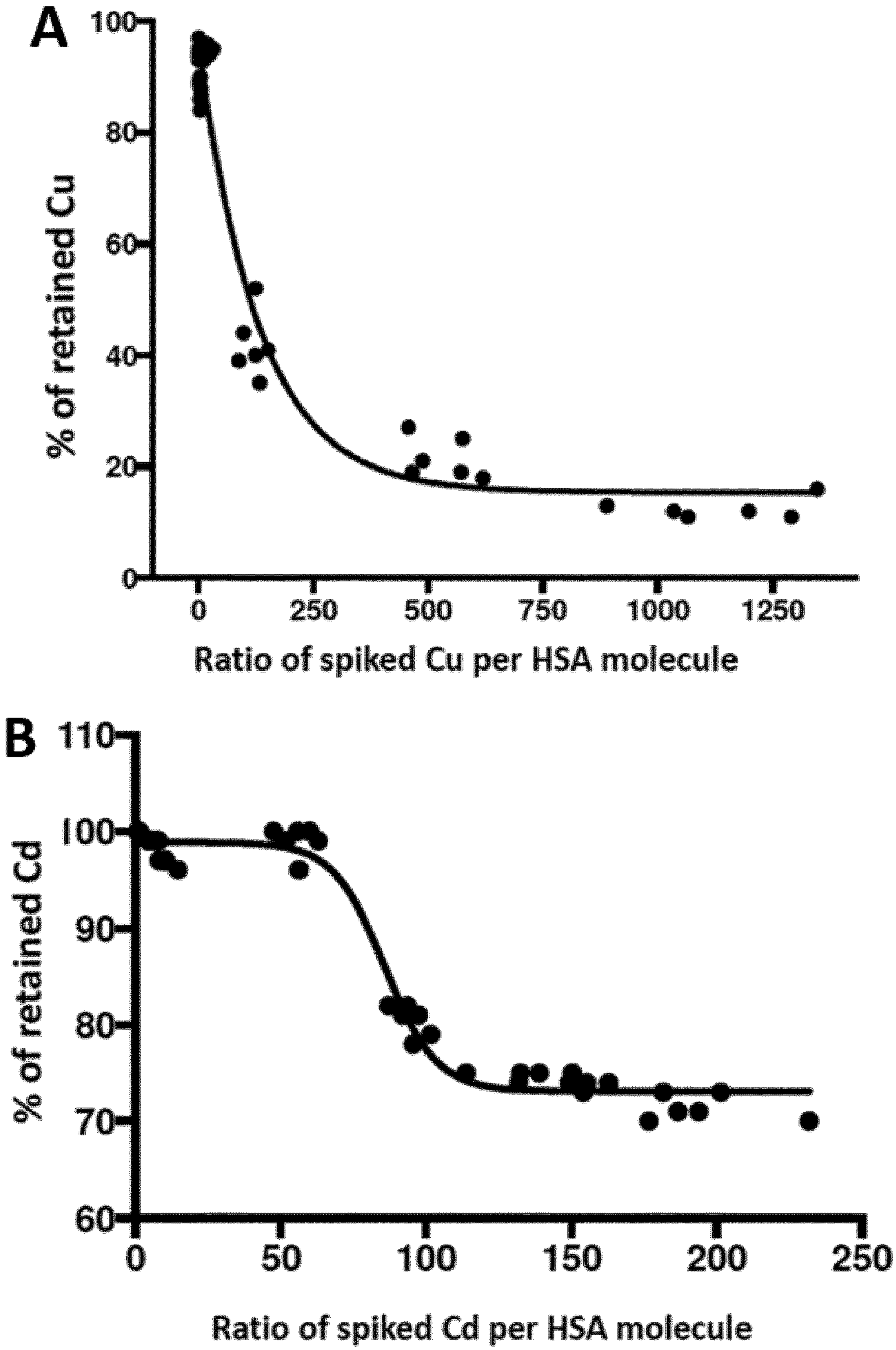

Specification includes a Sequence Listing.

(56) References Cited

OTHER PUBLICATIONS

Leblanc et al (Journal of Chromatography B, Sep. 15, 2018, 1095:87-93).*
Ramond et al (NELM, 1992, 326:507-512).*
Escobosa et al (Anal Bioanal. Chem. 2015, 407:1149-1157).*
Vierling (Clinical Gastroenterology and Hepatology 2015;13:2088-2108).*
Mansour et al (Hepatology, Apr. 2018, vol. 18, Suppl. s60-s65).*
Lagetta (2016 "Post-Transcriptional Changes in Serum Albumin: Role in the Pathogenesis of Bacterial Infections in Cirrhosis." Dissertation thesis, Alma Mater Studiorum University of Bologna).*
KR 20130078628 English translation of description.*
KR 20130078628 English translation of claims.*
Goumakos et al Abstract Only (Biochemistry and Cell Biology, vol. 69, Issue 12, pp. 809-820, abstract ).*
Sen et al (Journal of Physical Chemistry, 2011, 115:24037-24044).*
Ge et al: "Reduction in albumin binding function following liver resection in patients with and without cirrhosis", Translational Cancer Research, vol. 5, No. 6, pp. 756-764, Dec. 1, 2016.
Kalmmt et al: "Albumin-binding function is reduced in patients with decompensated cirrhosis and correlates Inversely with severity of liver disease assessed by model for end-stage liver disease", European Jouranl of Gastroenterology and Hepatology, vol. 19, No. 3, pp. 257-263, Jan. 1, 2007.
Naldi et al: "Structural and functional integrity of human serum albumin: Analytical approaches and clinical relevance in patients with liver cirrhosis", Journal of Pharmaceutical and Biomedial Analysis, vol. 144, pp. 138-153, Apr. 18, 2017.
Dettl et al: "Oxidative albumin damage in chronic liver failure: Relation to albumin binding capacity, liver dysfunction and survival", Journal of Hepatology, vol. 59, No. 5, pp. 978-983, Jun. 25, 2013.

* cited by examiner

METHODS AND KITS FOR DETECTING LIVER DYSFUNCTION IN A SUBJECT

FIELD OF THE INVENTION

The present invention relates to the methods and kits for detecting liver dysfunction in a subject, and uses thereof for diagnostic purposes.

BACKGROUND OF THE INVENTION

Most chronic liver diseases are notoriously asymptomatic, until cirrhosis with clinical decompensation occurs [1, 2]. Prevention of cirrhosis and the use of early diagnosis strategies, before and once it develops, are vital to maintain patients in a symptom-free state and to delay decompensation, and thus improve the outcome. This is particularly critical in liver transplanted patients. In early cirrhosis, conventional imaging and laboratory tests, often combined in scores, can lead to false-negative diagnosis [2]. Despite their lack of sensitivity and specificity, these tests are routinely used to explore the integrity of hepatocytes (aspartate transaminase and alanine transaminase), as well as the biliary (alkaline phosphatase and γ-glutamyltransferase) and synthesis (ammonia, prothrombin time and albumin) functions.

Since Human serum albumin (HSA) is exclusively synthesized and matured in the liver, not only its quantity (60% of all blood proteins normally) but also its quality may reflect liver dysfunction. Indeed, albumin exhibits a peculiar 3D structure, with multiple binding sites for multiple endogenous and exogenous ligands (it acts as the primary scavenger in blood).

Albumin undergoes several post-translational modifications in hepatocytes, including: acetylation, cysteinylation, homocysteinylation, glutathionylation, glycosylation, glycation, nitrosylation, nitration, phosphorylation and oxidation. The clinical relevance of some of these modifications has been recently investigated in advanced liver diseases (1-4) [1-4]. Such modifications in HSA structure translate in modifications of its conformation and binding properties [5]. This aspect has been exploited by Bar-Or et al. in cardiac ischemia, who proposed the albumin cobalt binding test (ACB) also known as the Ischemia Modified Albumin test (IMA) [6]. The IMA test is based on the fact that cardiac ischemia is associated with modifications in the structure of albumin and, thus, in the capacity of a specific binding site to bind cobalt. Since the approval of the IMA as a biomarker of cardiac ischemia by the FDA (Regulation number: 862.1215; http://www.accessdata.fda.gov), this test has also been investigated in liver diseases showing correlation with the severity of cirrhosis [7]. Briefly, the IMA test is performed by adding $CoCl_2$ and dithiothreitol to serum, followed by a colorimetric measurement of the (free-Co)-dithiothreitol complex at 470 nm. However, there still a need for additional biomarker of liver dysfunction.

SUMMARY OF THE INVENTION

The present invention relates to the methods and kits for detecting liver dysfunction in a subject, and uses thereof for diagnostic purposes. In particular, the present invention is defined by the claims.

DETAILED DESCRIPTION OF THE INVENTION

The first inventors' hypothesis is that all the principal HSA modifications, due to a diversity of liver diseases, can be indirectly revealed by investigating the binding capacity for different ligands. It was reported that each of the following ligands has a specific binding site on HSA: (i) gold (Au) binds preferentially to Cys34; (ii) copper (Cu) to the N-terminal binding site, (iii) cadmium (Cd) to the multi-metal binding site, (iv) L-thyroxine has 4 specific binding sites (Tr1-Tr4), and (v) dansylsarcosine was reported to bind to drug site 3 or to the diazepam-binding site [8]. Their second hypothesis is that modifications of the HSA conformation and binding properties appear at early stages of liver cell injuries, since HSA is exclusively synthesized and matured in hepatocytes.

Therefore, the inventors believe that the most frequent HSA structural modifications can be detected by measuring the free (unbound) ligands after spiking patient serum with solutions containing the abovementioned ligands. This is possible since Cu, Au and Cd cover the principal HSA binding sites, while dansylsarcosine and L-thyroxine could reflect its conformational modifications since their binding sites are located in the cavities of the protein. Thereafter, by revealing HSA modifications, liver dysfunction may be detected earlier than with conventional imaging or laboratory tests. Interestingly, all the cited ligands can be directly measured using a single method such as inductively coupled plasma mass spectrometry (ICP-MS) or inductively coupled plasma optical emission spectrometry (ICP-OES).

Based on these premises, the inventors present here the serum enhanced binding (SEB) test, a simple laboratory test of liver dysfunctions. The SEB test was developed by analyzing serum samples from patients with different liver diseases (diagnosed cirrhosis, patients with NASH without cirrhosis and liver transplant patients . . . ). Animal experimentations were also conducted to explore the precocity of HSA modifications in the course of chronic liver dysfunction.

Accordingly, the present invention relates to a method for determining whether a subject suffers or is at risk of suffering from a liver dysfunction comprising measuring a plurality of binding capacities to serum albumin wherein said measured plurality of binding capacities indicates whether the subject suffers or is at risk of suffering from a liver dysfunction.

In one embodiment, the plurality of binding capacities is compared with a predetermined reference value, and the detection of a difference between the plurality of binding capacities and the predetermined reference value indicates if the subject suffers or is at risk of suffering from a liver dysfunction.

In one embodiment, the invention relates to a method for determining whether a subject suffers or is at risk of suffering from a liver dysfunction comprising i) determining the binding capacity of serum albumin to at least one ligand, ii) comparing the binding capacity determined at step i) with a predetermined reference value, wherein detecting difference between the binding capacity determined at step i) and the predetermined reference value indicates whether the subject suffers or is at risk of suffering from a liver dysfunction As used herein, the term "subject" as used herein refers to any mammal organism. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered As used herein, the term "liver dysfunction" "or "hepatic dysfunction" refers to a state (e.g. the severity of the disease) in which the liver function is decreased relative to a normal state. Hepatic dysfunction is characteristic of liver diseases. A number of acute or chronic pathological conditions leads to liver dysfunction. These include, but are not limited to liver abscess, liver cancer, either primary or metastatic, cirrhosis, such as cirrhosis caused by the alcohol consumption or primary biliary cirrhosis, amebic liver abscess, autoimmune hepatitis, biliary atresia, coccidioidomycosis disseminated, portal hypertension hepatic infections (such as hepatitis A virus, hepatitis B virus, hepatitis C virus, hepatitis D virus, or hepatitis E virus), hemochromatosis, hepatocellular carcinoma, pyogenic liver abscess, Reye's syndrome, sclerosing cholangitis, Wilson's disease, drug induced hepatotoxicity, or fulminant or acute liver failure. In some embodiments, the liver is a non-alcoholic fatty liver disease. As used herein, the term "non-alcoholic fatty liver disease" has its general meaning in the art and is intended to refer to the spectrum of disorders resulting from an accumulation of fat in liver cells in individuals with no history of excessive alcohol consumption. In the mildest form, NAFLD refers to hepatic steatosis. The term NAFLD is also intended to encompass the more severe and advanced form non-alcoholic steatohepatitis (NASH), cirrhosis, hepatocellular carcinoma, and virus-induced (e.g., HIV, hepatitis) fatty liver disease. The term "NASH", as used herein, collectively refers to the state where the liver develops a hepatic disorder (e.g., inflammation, ballooning, fibrosis, cirrhosis, or cancer), or the state where the liver may induce such a pathological condition, and "NASH" is distinguished from "simple steatosis"; i.e., a condition in which fat is simply accumulated in the liver, and which does not progress to another hepatic-disorder-developing condition.

Accordingly, the method of the present invention is particularly suitable for determining whether a subject has or is at risk of having a liver disease.

Accordingly, the method of the present invention is also suitable for measuring the degree of severity of "liver dysfunction" "or "hepatic dysfunction".

As used herein, the term "risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. "Risk evaluation," or "evaluation of risk" in the context of the present invention encompasses making a prediction of the probability, odds, or likelihood that an event or disease state may occur, the rate of occurrence of the event or conversion from one disease state to another. Risk evaluation can also comprise prediction of future clinical parameters, traditional laboratory risk factor values, or other indices of relapse, either in absolute or relative terms in reference to a previously measured population. The methods of the present invention may be used to make continuous or categorical measurements of the risk of conversion, thus diagnosing and defining the risk spectrum of a category of subjects defined as being at risk of conversion. In the categorical scenario, the invention can be used to discriminate between normal and other subject cohorts at higher risk. In some embodiments, the present invention may be used so as to discriminate those at risk from normal.

In some embodiments, the method of diagnosing described herein is applied to a subject who presents symptoms of liver dysfunction without having undergone the routine screening to rule out all possible causes for liver dysfunction. The methods described herein can be part of the routine set of tests performed on a subject who presents symptoms of liver dysfunction such as jaundice, abdominal pain and swelling, swelling in the legs and ankles, itchy skin, dark urine color, pale stool color, bloody color stool, tar-colored stool, chronic fatigue, nausea or vomiting, loss of appetite, tendency to bruise easily . . . . The method of the present invention can be carried out in addition of other diagnostic tools that include ultrasound evaluation (e.g. elastography), biopsy and/or quantification of at least one further biomarkers such as levels of blood AST, ALT, ALP, TTT, ZTT, total bilirubin, total protein, albumin, lactate dehydrogenase, choline esterase and the like.

In some embodiments, the subject underwent a liver transplantation. As used herein, the term "liver transplantation" has the common meaning in the art and includes partial and whole liver transplantation in which a liver of a donor is partially or wholly resected and partially or wholly transplanted into a recipient. Partial liver transplantation is classified by operation mode into orthotopic partial liver transplantation, heterotopic partial liver transplantation, and the like, and the present invention can be applied to any of them. In partial liver transplantation, a liver transplant or a partial liver transplant from a donor corresponding to about 30-50% of the normal liver volume of a recipient is typically transplanted as a graft into the recipient whose liver has been wholly resected.

Accordingly, the present invention is particularly suitable for determining whether a liver transplant subject has or is at risk of having transplant rejection. The term "transplant rejection" as used herein is defined as functional and structural deterioration of the organ due to an active immune response expressed by the recipient, and independent of non-immunologic causes of organ dysfunction. The transplant rejection may be acute or chronic. The term "acute rejection" as used herein refers to a rejection of the transplanted organ developing after the first 5-60 post-transplant days. It is generally a manifestation of cell-mediated immune injury. It is believed that both delayed hypersensitivity and cytotoxicity mechanisms are involved. The immune injury is directed against HLA, and possibly other cell-specific antigens expressed by the tubular epithelium and vascular endothelium. The term "chronic rejection" as used herein refers to a rejection of the transplanted organ developing after the first 30-120 post-transplant days. The term "chronic rejection" also refers to a consequence of combined immunological injury (e.g. chronic rejection) and non-immunological damage (e.g. hypertensive nephrosclerosis, or nephrotoxicity of immunosuppressants like cyclosporine A), taking place month or years after transplantation and ultimately leading to fibrosis and sclerosis of the allograft, associated with progressive loss of kidney function.

In some embodiments, the method of the present invention is particularly suitable for determining whether a subject suffering from a liver disease achieves a response to a therapy. The method is thus particularly suitable for discriminating responder from non-responder. As used herein the term "responder" in the context of the present disclosure refers to a subject that will achieve a response, i.e. a subject who is under remission and more particularly a subject who does not suffer from liver dysfunction. A non-responder subject includes subjects for whom the disease does not show reduction or improvement after the treatment (e.g. the liver dysfunction remains stable or decreases). According to the present invention, the treatment consists in any method or drug that could be suitable for the treatment of liver dysfunction. Some liver problems can be treated with life-style modifications, such as stopping alcohol use or losing weight, typically as part of a medical program that includes careful monitoring of liver function. Each liver disease will have its own specific treatment regimen. For example, hepatitis A requires supportive care to maintain hydration while the body's immune system fights and resolves the infection. Patients with gallstones may require surgery to remove the gallbladder. Other diseases may need long-term medical care to control and minimize the consequences of their disease. In patients with cirrhosis and end-stage liver disease, medications may be required to control the amount of protein absorbed in the diet. Other examples include operations required to treat portal hypertension.

In some embodiments, when the liver transplant patient is at risk of transplant rejection, the treatment may consist in administering to the patient a therapeutically effective amount of an immunosuppressive treatment. As used herein, the term "immunosuppressive treatment" refers to any substance capable of producing an immunosuppressive effect, e.g., the prevention or diminution of the immune response and in particular the prevention or diminution of the production of Ig. Immunosuppressive drugs include, without limitation thiopurine drugs such as azathioprine (AZA) and metabolites thereof; nucleoside triphosphate inhibitors such as mycophenolic acid (Cellcept) and its derivative (Myfortic); derivatives thereof; prodrugs thereof; and combinations thereof. Other examples include but are not limited to 6-mercaptopurine ("6-MP"), cyclophosphamide, mycophenolate, prednisolone, sirolimus, dexamethasone, rapamycin, FK506, mizoribine, azothioprine and tacrolimus.

The method of the present invention is particularly suitable for monitoring the efficiency of a therapy. Typically a decrease of binding capacity (e.g. between measures performed at different time intervals) indicates that subject does not achieve a response with the therapy. Conversely an increase of binding capacity (e.g. between measures performed at different time intervals) indicates that subject achieves a response with the therapy.

The method of the present is also particularly suitable for evaluating the effects of drugs under development in producing liver injury during a preclinical or clinical studies.

As used herein, the term "serum albumin" has its general meaning in the art and refers to a globular protein that in humans is encoded by the ALB gene. Serum albumin is the most abundant plasma protein in mammals. Serum albumin is essential for maintaining the oncotic pressure needed for proper distribution of body fluids between intravascular compartments and body tissues. It also acts as a plasma carrier by non-specifically binding several hydrophobic steroid hormones and as a transport protein for hemin and fatty acids. Furthermore, serum albumin has a very long half-life of about 19 days, and its metabolism is well-known. Albumin has also been widely used as a protein stabilizer in commercial pharmaceuticals (Sangastino et al. (2012), Blood, 120(12) 2405-2411). An exemplary amino acid sequence for human serum albumin (HSA) is represented by SEQ ID NO:1 (UniProtKB/Swiss-Prot primary accession number P02768).

>sp|P02768|ALBU_HUMAN Serum albumin OS = *Homo sapiens* OX = 9606 GN = ALB PE = 1 SV = 2

SEQ ID NO: 1

```
MKWVTFISLLFLFSSAYSRGVFRRDAHKSEVAHRFKDLGEENFKALV
LIAFAQYLQQCPFEDHVKLVNEVTEFAKTCVADESAENCDKSLHTLF
GDKLCTVATLRETYGEMADCCAKQEPERNECFLQHKDDNPNLPRLVR
PEVDVMCTAFHDNEETFLKKYLYEIARRHPYFYAPELLFFAKRYKAA
FTECCQAADKAACLLPKLDELRDEGKASSAKQRLKCASLQKFGERAF
KAWAVARLSQRFPKAEFAEVSKLVTDLTKVHTECCHGDLLECADDRA
DLAKYICENQDSISSKLKECCEKPLLEKSHCIAEVENDEMPADLPSL
AADFVESKDVCKNYAEAKDVFLGMFLYEYARRHPDYSVVLLLRLAKT
YETTLEKCCAAADPHECYAKVFDEFKPLVEEPQNLIKQNCELFEQLG
EYKFQNALLVRYTKKVPQVSTPTLVEVSRNLGKVGSKCCKHPEAKRM
PCAEDYLSVVLNQLCVLHEKTPVSDRVTKCCTESLVNRRPCFSALEV
DETYVPKEFNAETFTFHADICTLSEKERQIKKQTALVELVKHKPKAT
KEQLKAVMDDFAAFVEKCCKADDKETCFAEEGKKLVAASQAALGL
```

As used herein, the term "ligand" refers to any molecule that has a specific binding site on albumin. In some embodiments, the ligand is selected from the group consisting of gold (Au), copper (Cu), cadmium (cd), L-thyroxine and dansylsarcosine.

As used herein, the term "binding capacity" refers to the amount of the ligand that the serum albumin can bind under equilibrium conditions if every available binding site on the protein is utilized.

Typically, the method of the present invention is carried out as follows. In a first step a serum sample obtained from the subject is prepared. As used herein, the term "serum sample" relates to a sample wherein a blood sample is tapped into a dry-glass, left to coagulate at room temperature, and after which they are centrifuged. Then the serum sample is exposed to a predetermined amount of the ligand for a time sufficient for allowing the serum albumin to bind to said ligand. In some embodiments, the time of exposure can be varied for about 1, 5 or 10 seconds, or about 1, 2, 3, 5, 10, 20 or 30 minutes, or about 1, 2, 3 or 5 hours. In a third step, the amount of the free (unbound) ligand is then measured in the sample, wherein said measure indicates the binding capacity of the serum albumin. Optionally a ratio between the free amount and the concentration of the serum albumin is calculated, wherein said ratio indicates the binding capacity of the serum albumin. Optionally, the protein contained in the sample are separated from the sample before measuring the amount of the free ligand. Typically said separation may consist in a centrifugation.

In some embodiments, the binding capacity for 1, 2, 3, 4, 5, or 6 ligands is measured.

In one embodiment, the binding capacity of gold (Au) is measured. In one embodiment, the binding capacity of copper (Cu) is measured. In one embodiment, the binding capacity of cadmium (cd) is measured. In one embodiment, the binding capacity of L-thyroxine is measured. In one embodiment, the binding capacity of dansylsarcosine is measured. In one embodiment, the binding capacities of gold and copper are measured. In one embodiment, the binding capacities of gold and cadmium are measured. In one embodiment, the binding capacities of gold and L-thyroxine are measured. In one embodiment, the binding capacities of gold and dansylsarcosine are measured. In one embodiment, the binding capacities of copper and cadmium are measured. In one embodiment, the binding capacities of copper and L-thyroxine are measured. In one embodiment, the binding capacities of copper and dansylsarcosine are measured. In one embodiment, the binding capacities of cadmium and L-thyroxine are measured. In one embodiment, the binding capacities of cadmium and dansylsarcosine are measured. In one embodiment, the binding capacities of L-thyroxine and dansylsarcosine are measured. In one embodiment, the binding capacities of gold, copper and cadmium are measured. In one embodiment, the binding capacities of gold, copper and L-thyroxine are measured. In one embodiment, the binding capacities of gold, copper and dansylsarcosine are measured. In one embodiment, the binding capacities of gold, L-thyroxine and dansylsarcosine are measured. In one embodiment, the binding capacities of gold, L-thyroxine and cadmium are measured. In one embodiment, the binding capacities of gold, cadmium and dansylsarcosine are measured. In one embodiment, the binding capacities of copper, cadmium and L-thyroxine are measured. In one embodiment, the binding capacities of copper, cadmium and dansylsarcosine are measured. In one embodiment, the binding capacities of copper, L-thyroxine and dansylsarcosine are measured. In one embodiment, the binding capacities of L-thyroxine, cadmium and dansylsarcosine are measured. In one embodiment, the binding capacities of gold, copper, L-thyroxine and cadmium are measured. In one embodiment, the binding capacities of gold, copper, L-thyroxine and dansylsarcosine are measured. In one embodiment, the binding capacities of gold, copper, cadmium and dansylsarcosine are measured. In one embodiment, the binding capacities of copper, L-thyroxine, cadmium and dansylsarcosine are measured. In one embodiment, the binding capacities of gold, copper, L-thyroxine, cadmium and dansylsarcosine are measured.

Accordingly, 1, 2, 3, 4, or 5 serum samples are prepared separately and each exposed to a particular amount of the corresponding ligand. In some embodiments, 1, 2, 3, 4 or 5 container (e.g. tubes) containing an amount of the corresponding ligand are prepared. The sample serum is then added to the container and finally after separating the proteins contained in the sample typically by a centrifugation the amount of the free ligand is measured in the resting sample.

In some embodiments, the binding capacity (e.g. the amount of the free ligand) is determined by mass spectrometry.

As used herein, the term "Child-Pugh score" refers to a system for assessing the prognosis, including the required strength of treatment and necessity of liver transplant, of chronic liver disease, primarily cirrhosis. It provides a forecast of the increasing severity of your liver disease and your expected survival rate. The Child-Pugh score is defined by different class: "Class A" (CA) for least severe liver disease, "Class B (CB) for moderately severe liver disease, "Class C" (CC) for most severe liver disease.

As used herein, the term "mass spectrometry" or "MS" refers to an analytical technique to identify compounds by their mass. MS refers to methods of filtering, detecting, and measuring ions based on their m/z. MS technology generally includes (1) ionizing the compounds to form charged species (e.g., ions); and (2) detecting the molecular weight of the ions and calculating their m/z. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 2:264-76 (1999); and Merchant and Weinberger, Electrophoresis 21:1164-67 (2000).

Typically the serum samples are processed to obtain preparations that are suitable for analysis by mass spectrometry. Such purification will usually include chromatography, such as liquid chromatography or capillary electrophoresis, and may also often involve an additional purification procedure that is performed prior to chromatography. Various procedures may be used for this purpose depending on the type of sample or the type of chromatography. Examples include filtration, centrifugation, combinations thereof and the like. The pH of the serum sample may then be adjusted. The sample may be purified with a filtration. The filtrate from this filtration can then be purified by liquid chromatography and subsequently subjected to mass spectrometry analysis. Various methods have been described involving the use of high performance liquid chromatography (HPLC) for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000). Commercially available HPLC columns include, but are not limited to, polar, ion exchange (both cation and anion), hydrophobic interaction, phenyl, C-2, C-8, C-18, and polar coating on porous polymer columns. During chromatography, the separation of materials is effected by variables such as choice of eluent (also known as a "mobile phase"), choice of gradient elution and the gradient conditions, temperature, etc.

In some embodiments, the ligands are ionized by any method known to the skilled artisan. Mass spectrometry is performed using a mass spectrometer, which includes an ion source for ionizing the fractionated sample and creating charged molecules for further analysis. Ionization sources used in various MS techniques include, but are not limited to, electron ionization, chemical ionization, electrospray ionization (ESI), photon ionization, atmospheric pressure chemical ionization (APCI), photoionization, atmospheric pressure photoionization (APPI), fast atom bombardment (FAB)/liquid secondary ionization (LSIMS), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc. After the sample has been ionized, the positively charged ions thereby created may be analyzed to determine m/z. Suitable analyzers for determining m/z include quadrupole analyzers, ion trap analyzers, and time-of-flight analyzers. The ions may be detected using one of several detection modes. For example, only selected ions may be detected using a selective ion monitoring mode (SIM), or alternatively, multiple ions may be detected using a scanning mode, e.g., multiple reaction monitoring (MRM) or selected reaction monitoring (SRM). One may enhance the resolution of the MS technique by employing "tandem mass spectrometry," or "MS/MS." In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples. Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps may be combined in methods known as "MS/MS". Various other combinations may be employed, such as MS/MS/TOF, MALDI/MS/MS/TOF, or SELDI/MS/MS/TOF mass spectrometry.

In some embodiments, since most of the ligands are metals, ICP-MS may be preferred. Inductively coupled plasma mass spectrometry (ICP-MS) is a type of mass spectrometry which is capable of detecting metals and several non-metals at concentrations as low as one part in $10^{15}$ (part per quadrillion, ppq) on non-interfered low-background isotopes. This is achieved by ionizing the sample with inductively coupled plasma and then using a mass spectrometer to separate and quantify those ions. Inductively coupled plasma optical emission spectrometry (ICP-OES), is an analytical technique used for the detection of chemical elements. It is a type of emission spectroscopy that uses the inductively coupled plasma to produce excited atoms and ions that emit electromagnetic radiation at wavelengths characteristic of a particular element. It is a flame technique with a flame temperature in a range from 6000 to 10000 K. The intensity of this emission is indicative of the concentration of the element within the sample.

One or more steps of the methods may be performed using automated machines. In some embodiments, one or more purification steps are performed on-line, and more preferably all of the LC purification and mass spectrometry steps may be performed in an on-line fashion.

Typically, the predetermined reference value is a threshold value or a cut-off value, which can be determined experimentally, empirically, or theoretically. A threshold value can also be arbitrarily selected based upon the existing experimental and/or clinical conditions, as would be recognized by a person of ordinary skilled in the art. For example, retrospective measurement of the binding capacity in properly banked historical samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the binding capacity in a group of reference, one can use algorithmic analysis for the statistic treatment of the expression levels determined in samples to be tested, and thus obtain a classification standard having significance for sample classification.

The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, a score which is a composite of the measured binding capacities is determined and compared to a reference value wherein a difference between said score and said reference value indicates whether the subject suffers or is at risk of suffering from a liver dysfunction. As used herein, the term "score" refers to a piece of information, usually a number that conveys the result of the subject on a test. A risk scoring system separates a patient population into different risk groups; herein the process of risk stratification classifies the patients into very high-risk, high-risk, intermediate-risk and low-risk groups.

In some embodiments, the method of the invention comprises the use of a classification algorithm. As used herein, the term "algorithm" is any mathematical equation, algorithmic, analytical or programmed process, or statistical technique that takes one or more continuous parameters and calculates an output value, sometimes referred to as an "index" or "index value." Non-limiting examples of algorithms include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining parameters are linear and non-linear equations and statistical classification analyses to determine the relationship between levels of said parameters and the risk of allograft loss. Of particular interest are structural and syntactic statistical classification algorithms, and methods of risk index construction, utilizing pattern recognition features, including established techniques such as cross-correlation, Principal Components Analysis (PCA), factor rotation, Logistic Regression (Log Reg),Linear Discriminant Analysis (LDA), Eigengene Linear Discriminant Analysis (ELDA), Topological Data Analysis (TDA), Neural Networks, Support Vector Machine (SVM) algorithm and Random Forests algorithm (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, Recommender System Algorithm and Hidden Markov Models, among others. Other techniques may be used in survival and time to event hazard analysis, including Cox, Weibull, Kaplan-Meier and Greenwood models well known to those of skill in the art.

As used herein, the term "classification algorithm" has its general meaning in the art and refers to classification and regression tree methods and multivariate classification well known in the art such as described in U.S. Pat. No. 8,126,690; WO2008/156617.

In some embodiments, the method of the present invention comprises the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting (e.g. XGBoost). Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models. The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering. In some instances, the machine learning algorithms comprise a reinforcement learning algorithm Examples of reinforcement learning algorithms include, but are not limited to, temporal difference learning, Q-learning and Learning Automata. Alternatively, the machine learning algorithm may comprise Data Pre-processing. In some embodiments, the boosting model includes the XGBoost algorithm.

Thus, in some embodiments, the method of the present invention comprises a) measuring a plurality of binding capacities (i.e. 2, 3, 4 or 5); b) implementing a classification algorithm on data comprising the measured binding capacities so as to obtain an algorithm output; c) determining the probability that the subject suffers from a liver dysfunction.

In some embodiments, the algorithm is implemented on a computer using well-known computer processors, memory units, storage devices, computer software, and other components. Typically, the computer contains a processor, which controls the overall operation of the computer by executing computer program instructions which define such operation. The computer program instructions may be stored in a storage device (e.g., magnetic disk) and loaded into memory when execution of the computer program instructions is desired. The computer also includes other input/output devices that enable user interaction with the computer (e.g., display, keyboard, mouse, speakers, buttons, etc.). One skilled in the art will recognize that an implementation of an actual computer could contain other components as well.

In some embodiments, the algorithm is implemented using computers operating in a client-server relationship. Typically, in such a system, the client computers are located remotely from the server computer and interact via a network. The client-server relationship may be defined and controlled by computer programs running on the respective client and server computers. In some embodiments, the results may be displayed on the system for display, such as with LEDs or an LCD. Accordingly, in some embodiments, the algorithm can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet. The computing system can include clients and servers. A client and server are generally remote from each other and typically interact through a communication network. The relationship of client and server arises by virtue of computer programs running on the respective computers and having a client-server relationship to each other.

In some embodiments, the algorithm is implemented within a network-based cloud computing system. In such a network-based cloud computing system, a server or another processor that is connected to a network communicates with one or more client computers via a network. A client computer (e.g. a mobile device, such as a phone, tablet, or laptop computer) may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For instance, the physician may register the parameters (i.e. input data) on, which then transmits the data over a long-range communications link, such as a wide area network (WAN) through the Internet to a server with a data analysis module that will implement the algorithm and finally return the output (e.g. score) to the mobile device.

In some embodiments, the output results can be incorporated in a Clinical Decision Support (CDS) system. These output results can be integrated into an Electronic Medical Record (EMR) system.

A further object of the present invention relates to a kit or device for performing the method of the present invention, comprising means for determining the binding capacity(ies) as described above. In some embodiments, the kits or devices of the present invention comprise at least one sample collection container for sample collection. Collection devices and container include but are not limited to syringes, lancets, BD VACUTAINER® blood collection tubes. In some embodiments, the container contains a predetermined amount of the ligand. In some embodiments, the kits or devices described herein further comprise instructions for using the kit or device and interpretation of results. In some embodiments, the kit or device of the present invention further comprises a microprocessor to implement an algorithm so as to determine the probability that the patient suffers from a liver dysfunction. In some embodiments, the kit or device of the present invention further comprises a visual display and/or audible signal that indicates the probability determined by the microprocessor. In some embodiments, the kit or device of the present invention comprises: i) a mass spectrometer; ii) a receptacle into which the serum sample is placed, and which is connectable to the mass spectrometer so that the mass spectrometer can quantify the amount of the free ligand; iii) optionally a microprocessor to implement an algorithm on data so as to determine the probability that the subject suffers from a liver dysfunction and iv) a visual display and/or audible signal that indicates the probability determined by the microprocessor.

The invention will be further illustrated by the following figures and examples. However, these examples and figures should not be interpreted in any way as limiting the scope of the present invention.

FIGURES

Figures 1C, 1D:
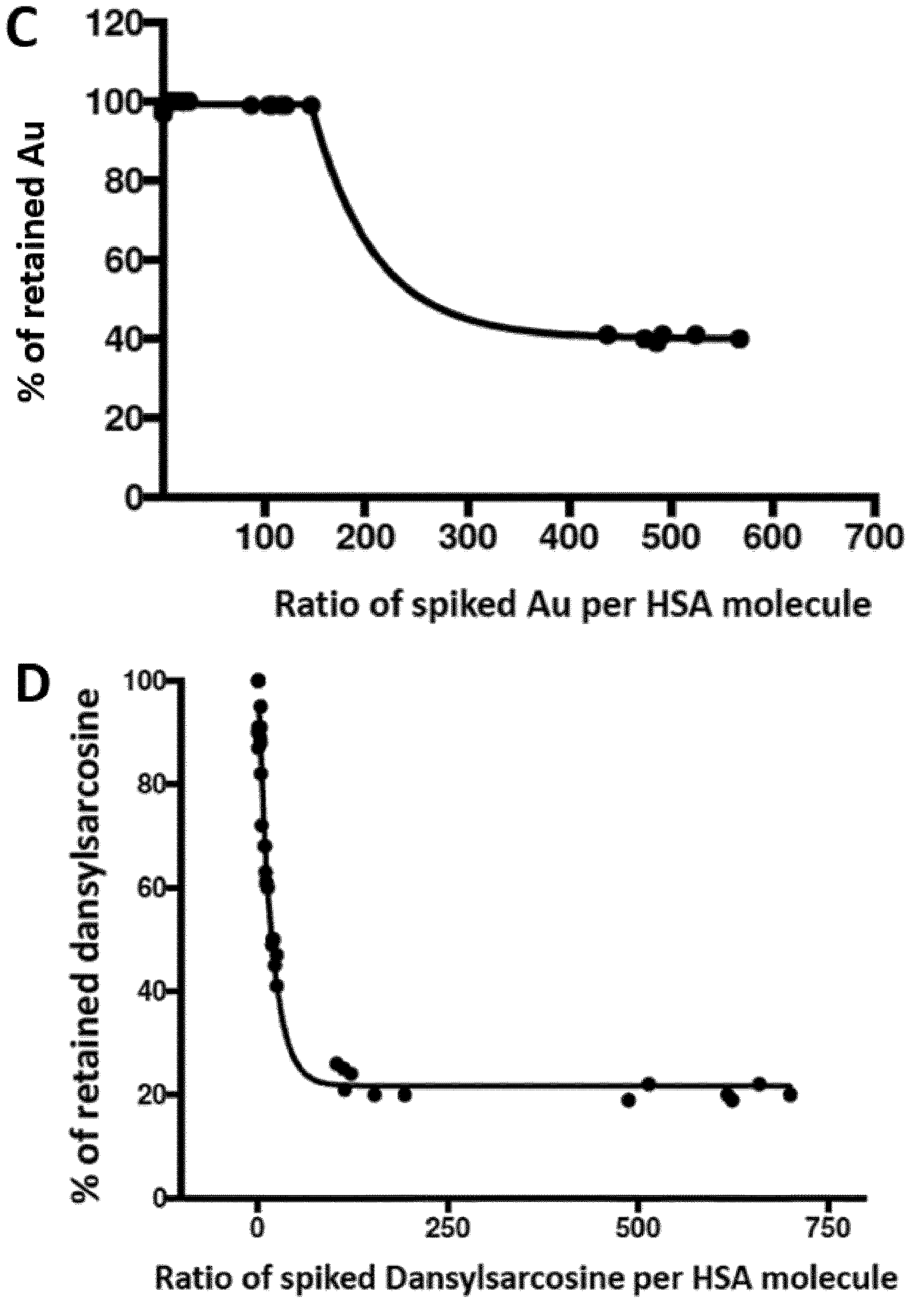

FIG. 1. (A-D) Serum enhanced binding of Cu, Cd, Au and dansylsarcosine.

Figures 2A, 2B:
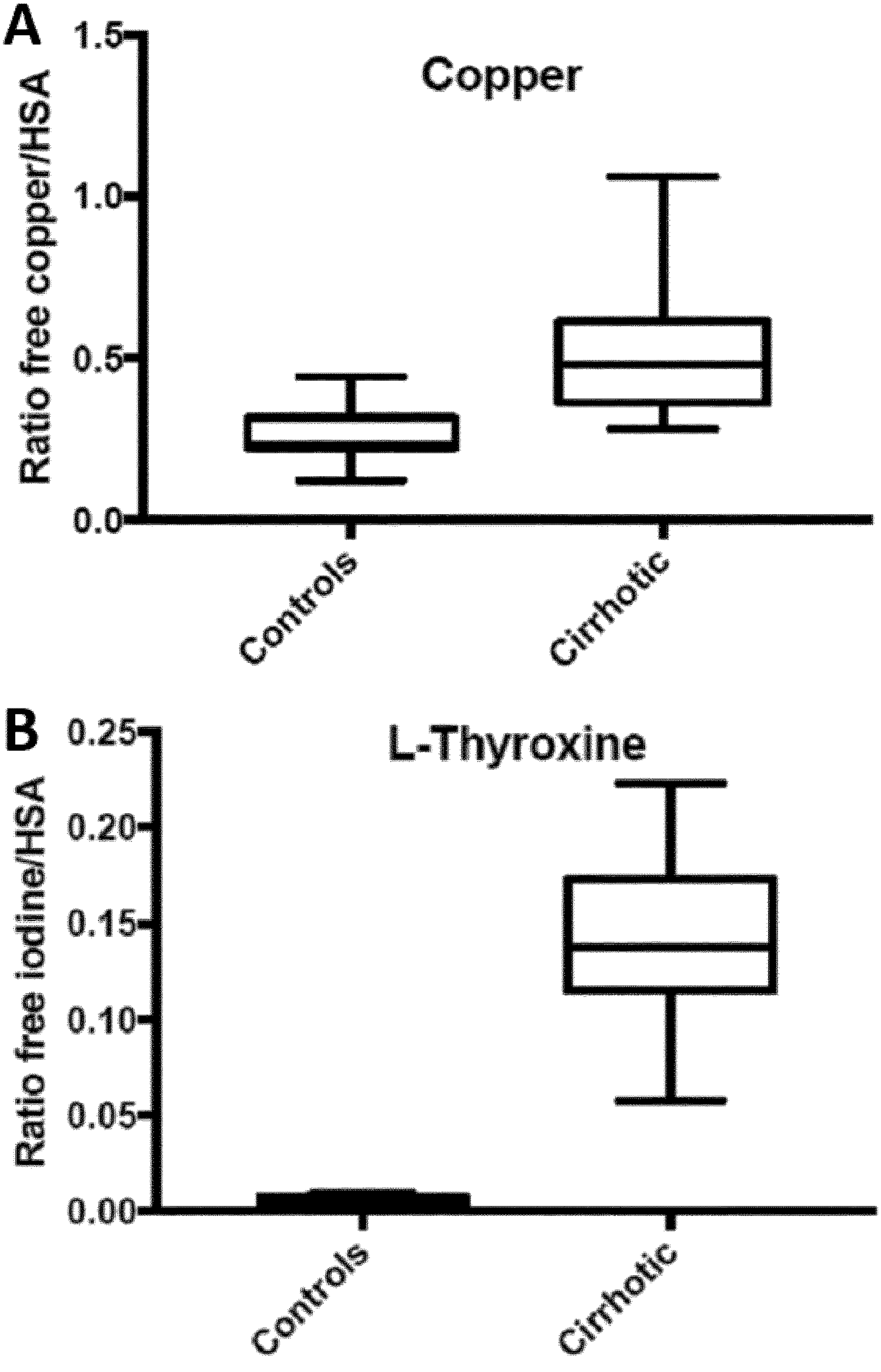
Figures 2C, 2D:
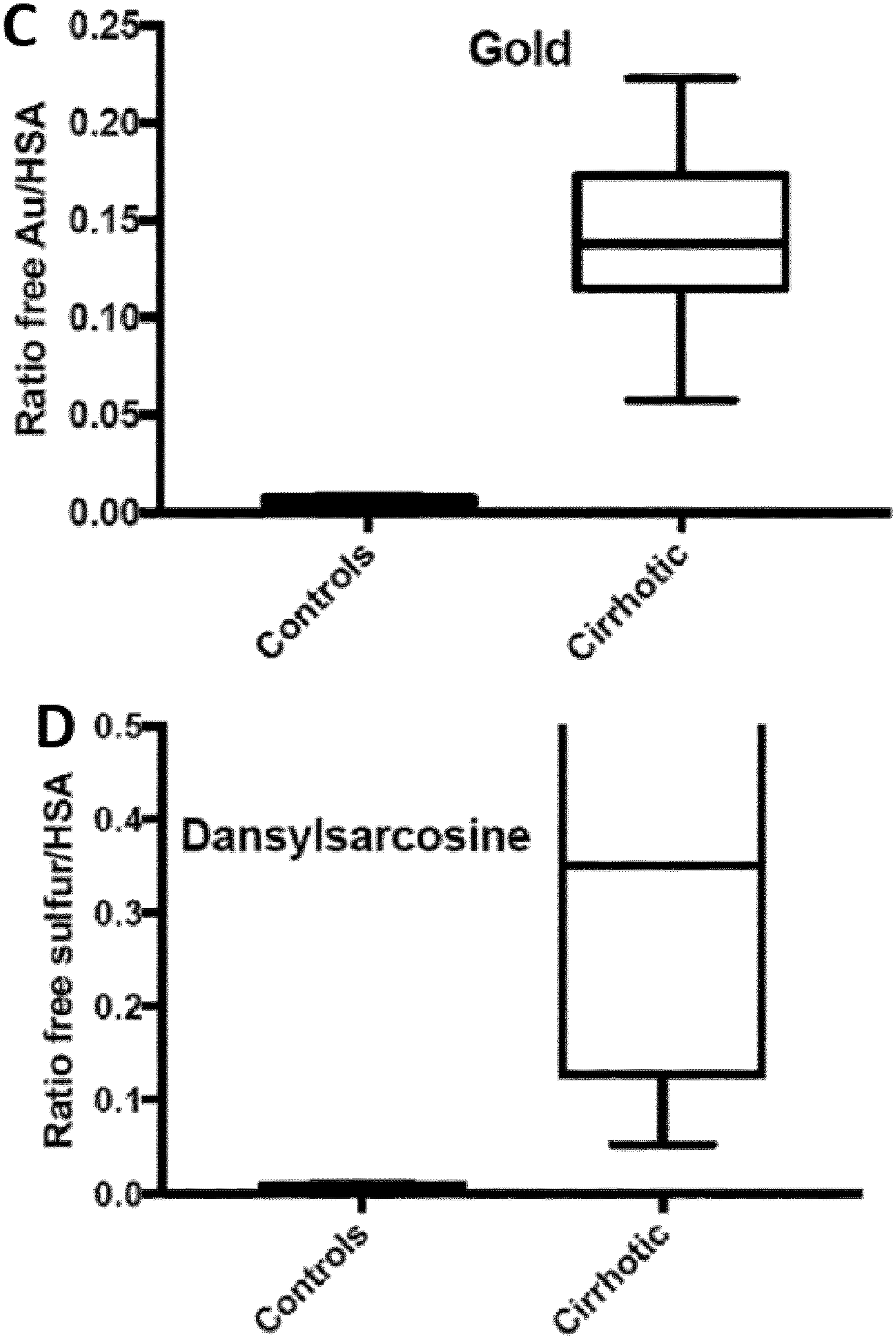

FIG. 2. (A-D) Discrimination between control patients with no liver disease and cirrhotic patients by the SEB test. Ligands were spiked to serums using solutions at the following concentrations, expressed as HSA/ligand ratios (namely 1 molecule of HSA for X atoms or molecules of ligand): Cu 1/10, L-thyroxine 1/10, Au 1/100, dansylsarcosine 1/5. Cu was tested in 18 patients, Au in 16 patients, L-thyroxine in 16 patients and dansylsarcosine in 6 patients only. The ordinates represent the (μM of free ligand)/(μM of HSA) ratio.

Figure 3:
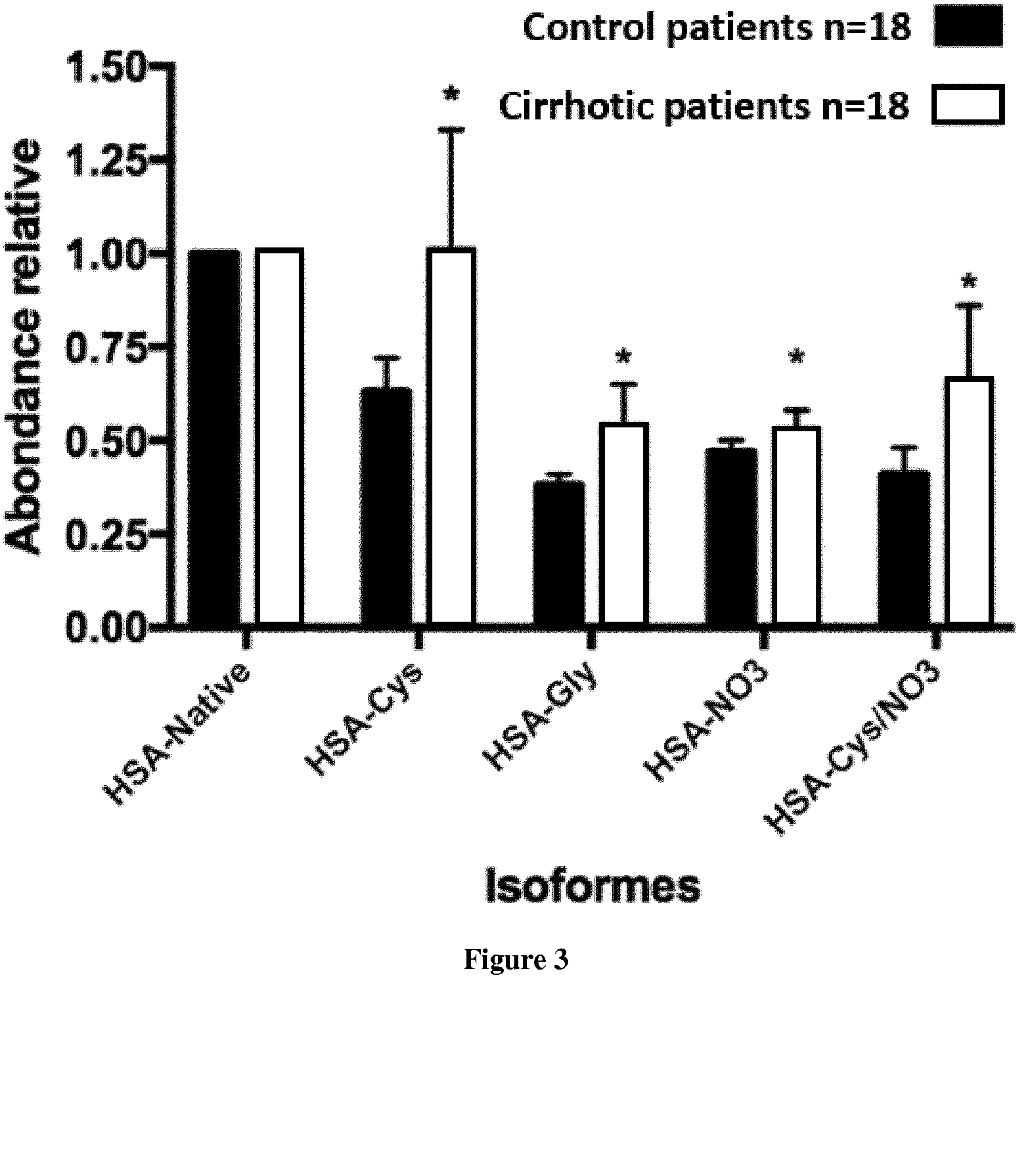

FIG. 3. Determination of HSA isoforms in 18 cirrhotic and 18 control patients. Observation of high abundances of HSA isoforms in all cirrhotic patients.

Figures 4A, 4B:
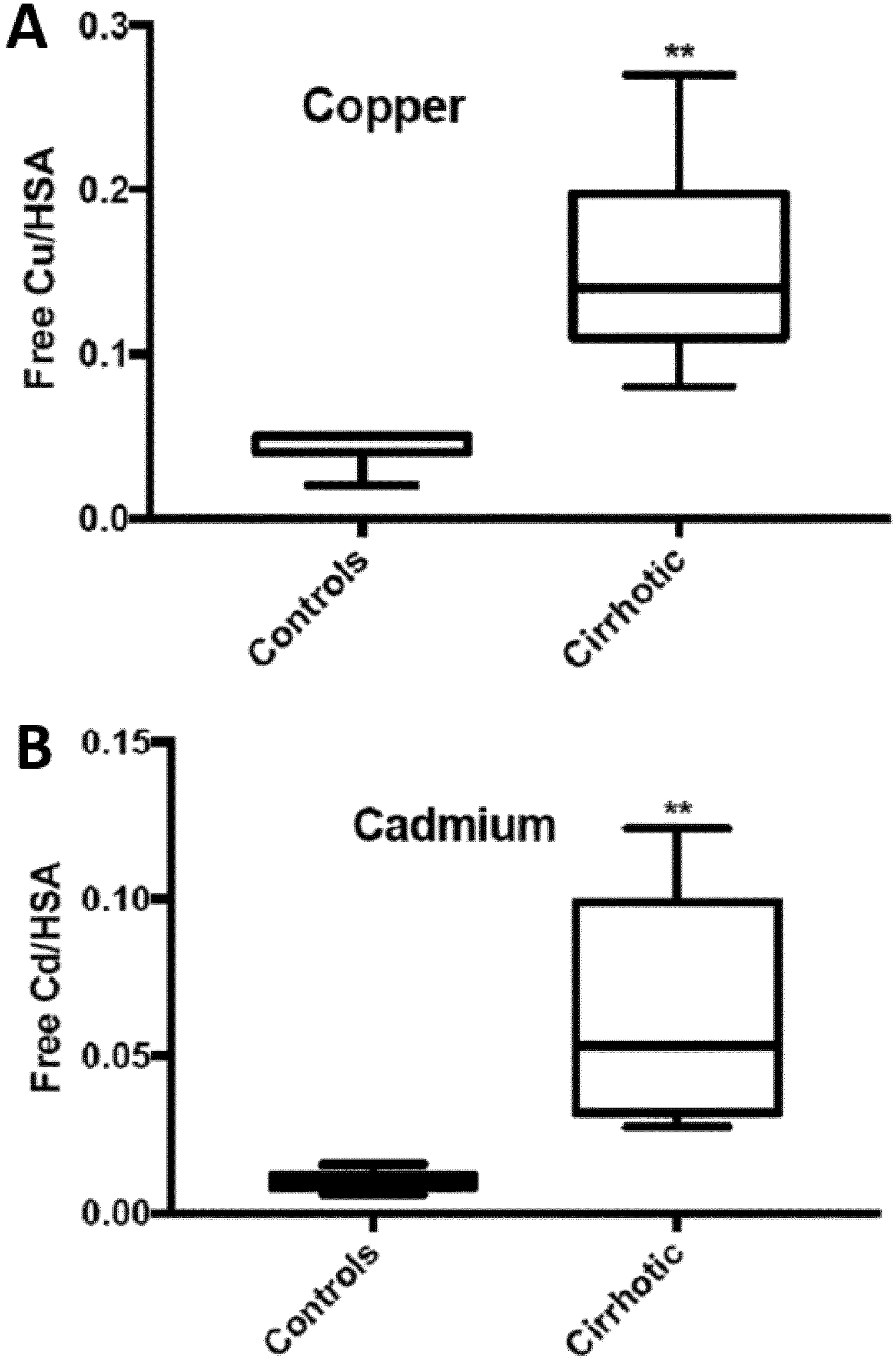
Figures 4C, 4D:
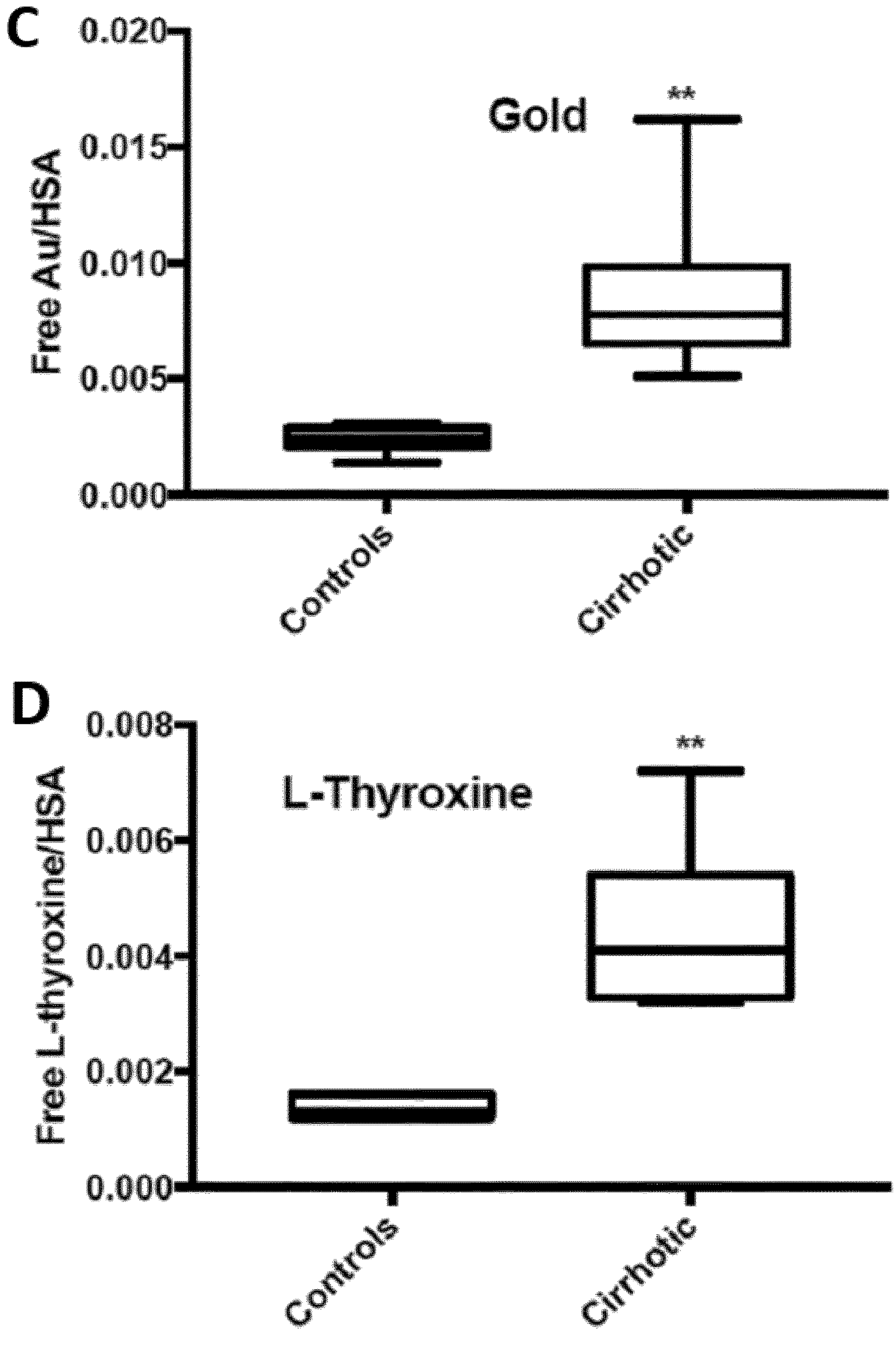

FIG. 4. (A-D) Discrimination between non-cirrhotic and cirrhotic patients by the SEB test with lower concentrations for Au, Cu and L-thyroxine. Cd was also tested in this group at a ratio of 1/5 (HAS/Cd). ** means $p<0.001$. n=12 for all ligands in both groups except L-thyroxine where n=6.

Figures 5A, 5B:
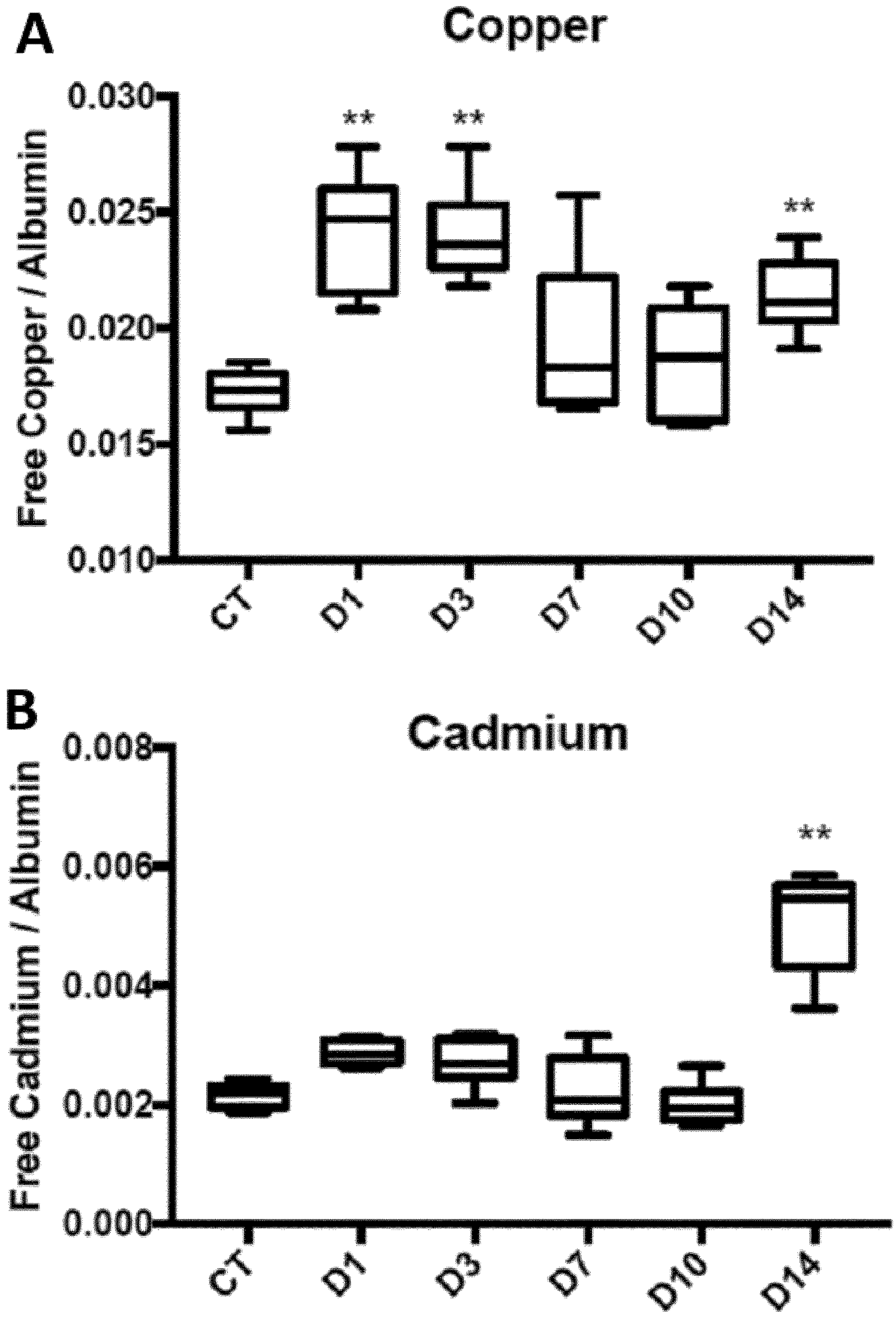
Figure 5C:
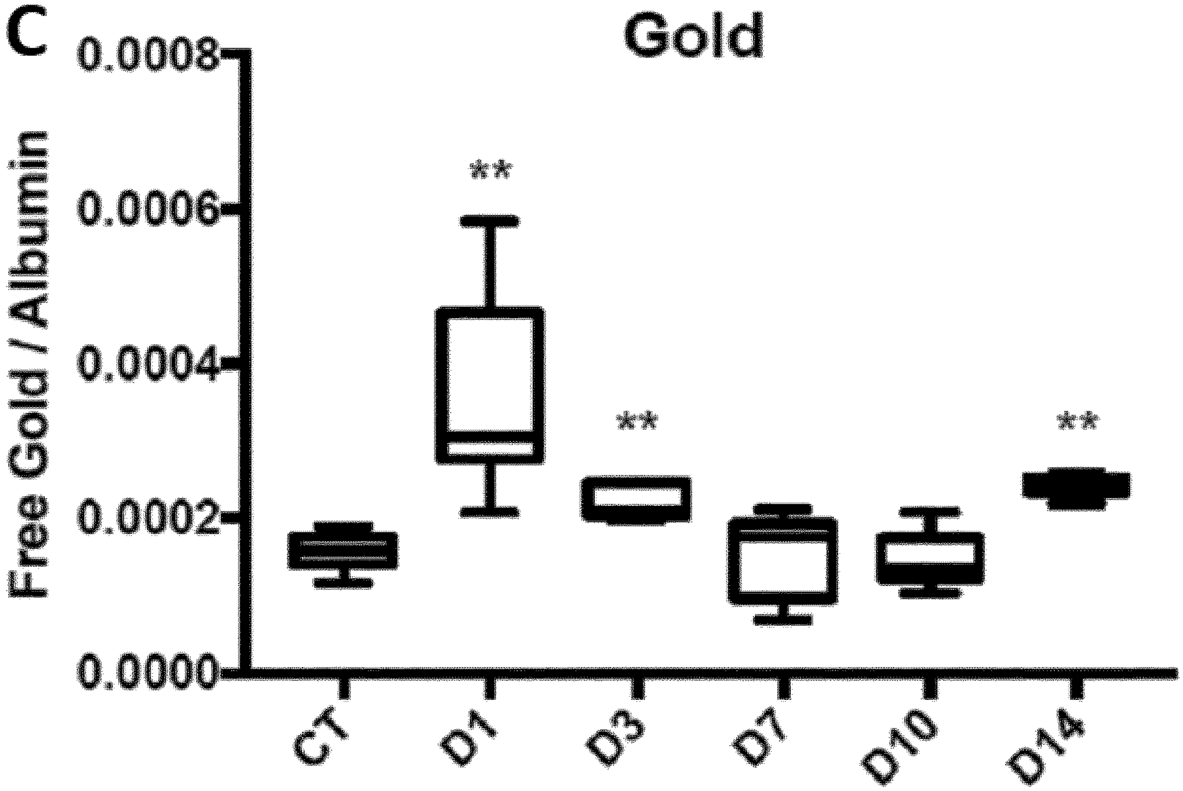
Figure 5D:
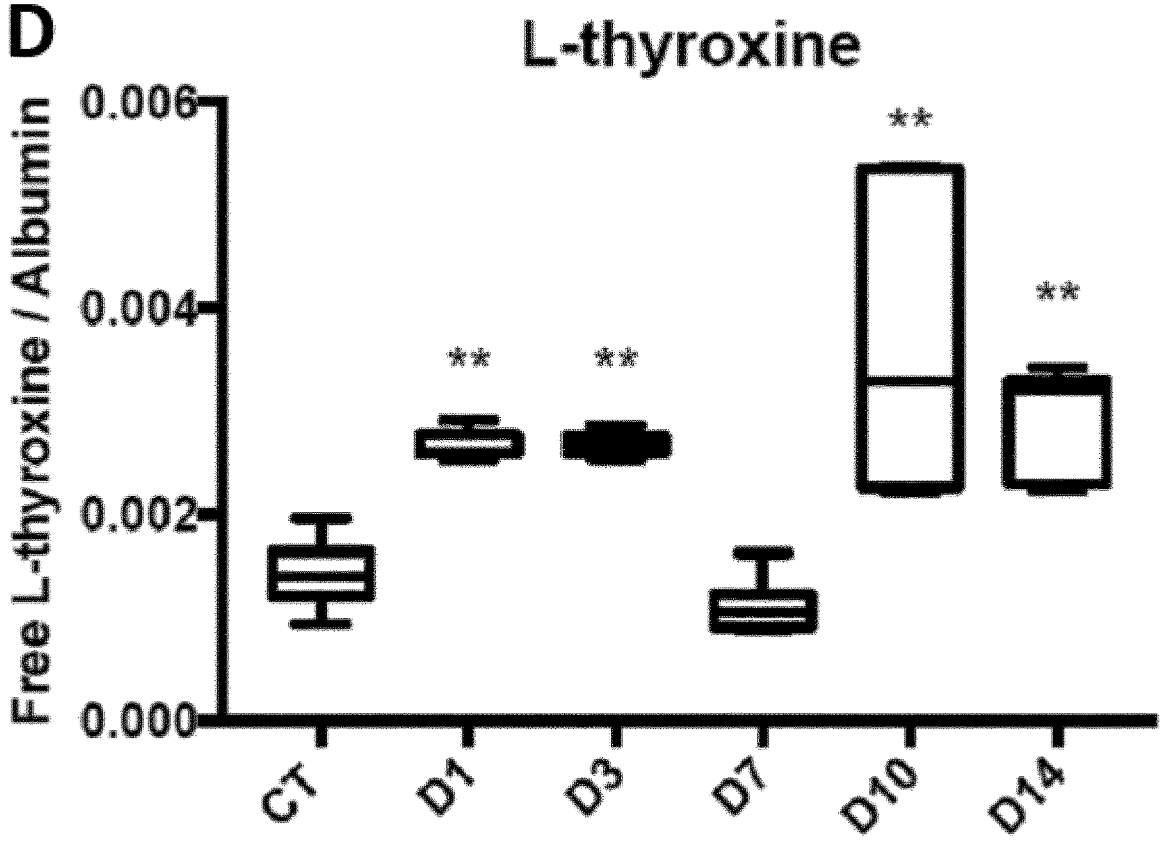

FIG. 5. (A-D) Time evolution of ligand binding in rats after daily administration for 1, 3, 7, 10 and 14 days of high doses of ethanol. The groups of rats (n=9 each) D1, D3, D7, D10 and D14 received 0.4 g of ethanol for 1, 3, 7, 10 and 14 days respectively. *=$p<0.05$; ** $p<0.01$.

Figures 6A, 6B:
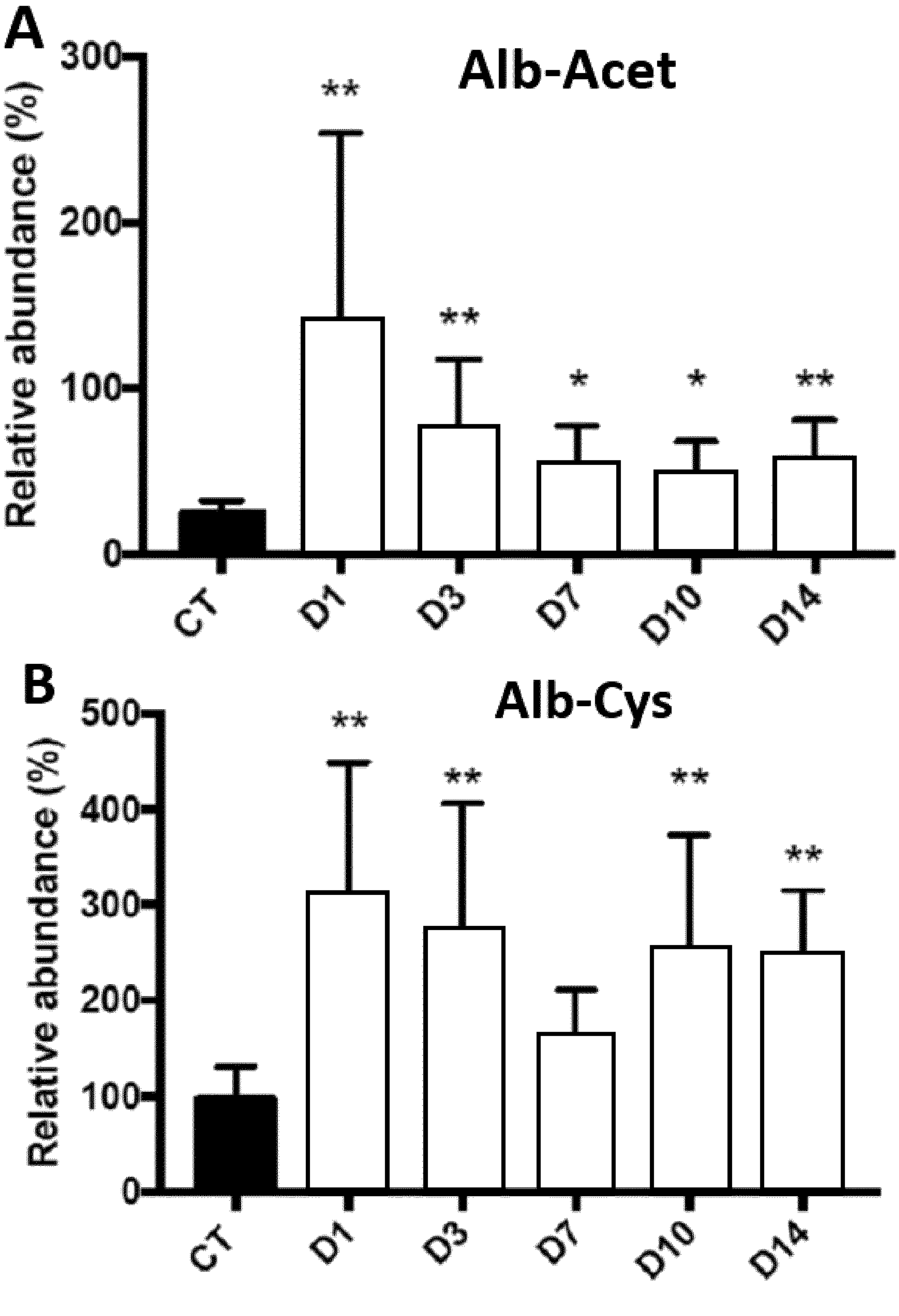
Figures 6C, 6D:
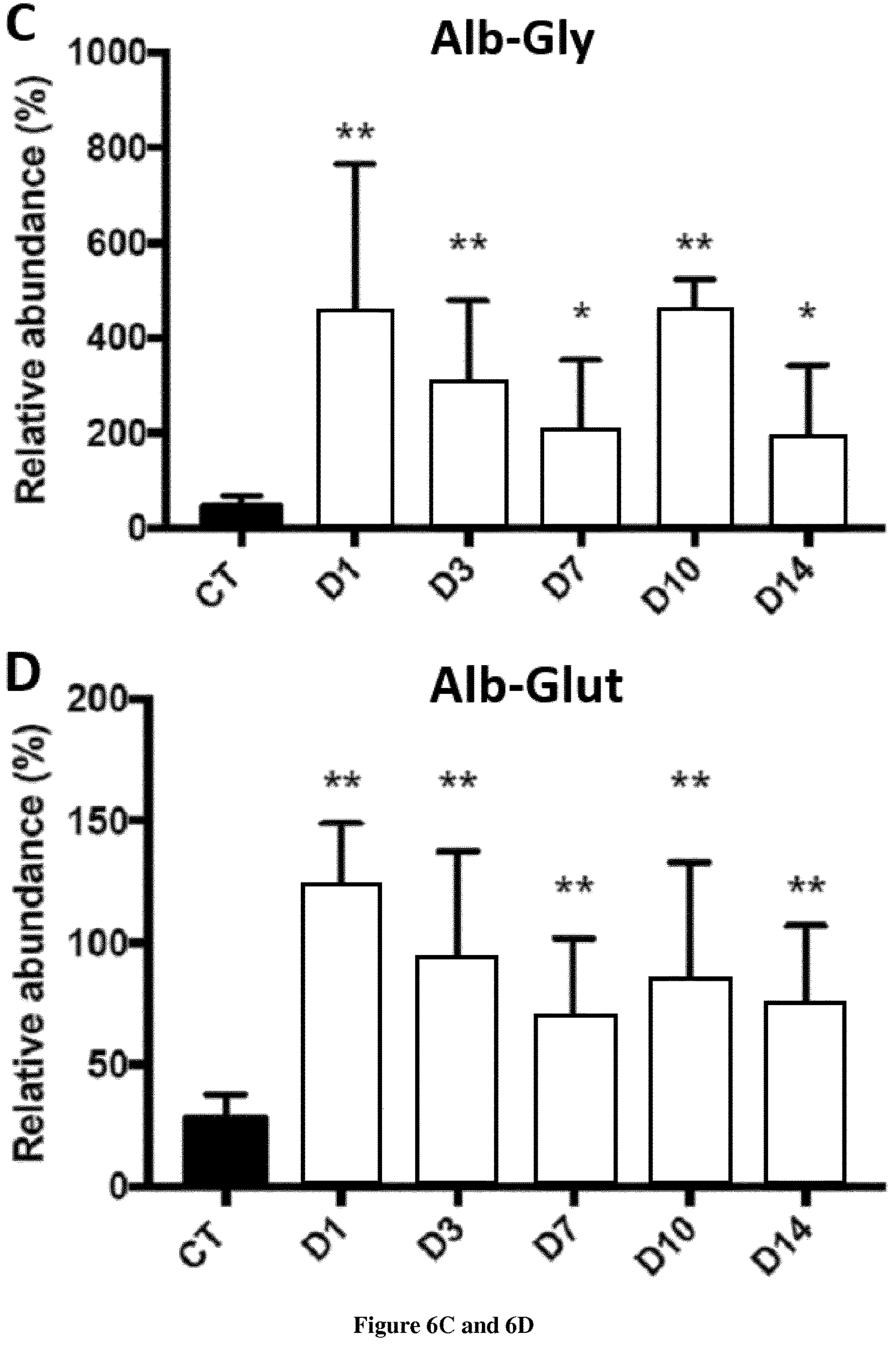
Figure 7A:
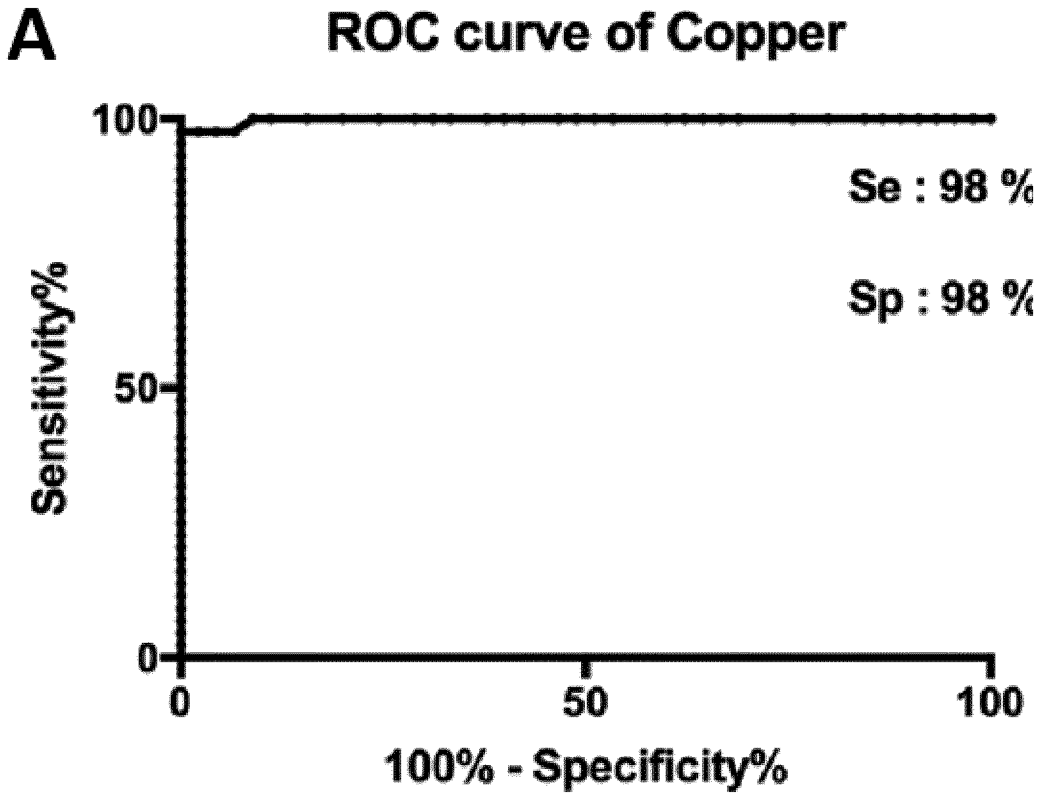
Figure 7B:
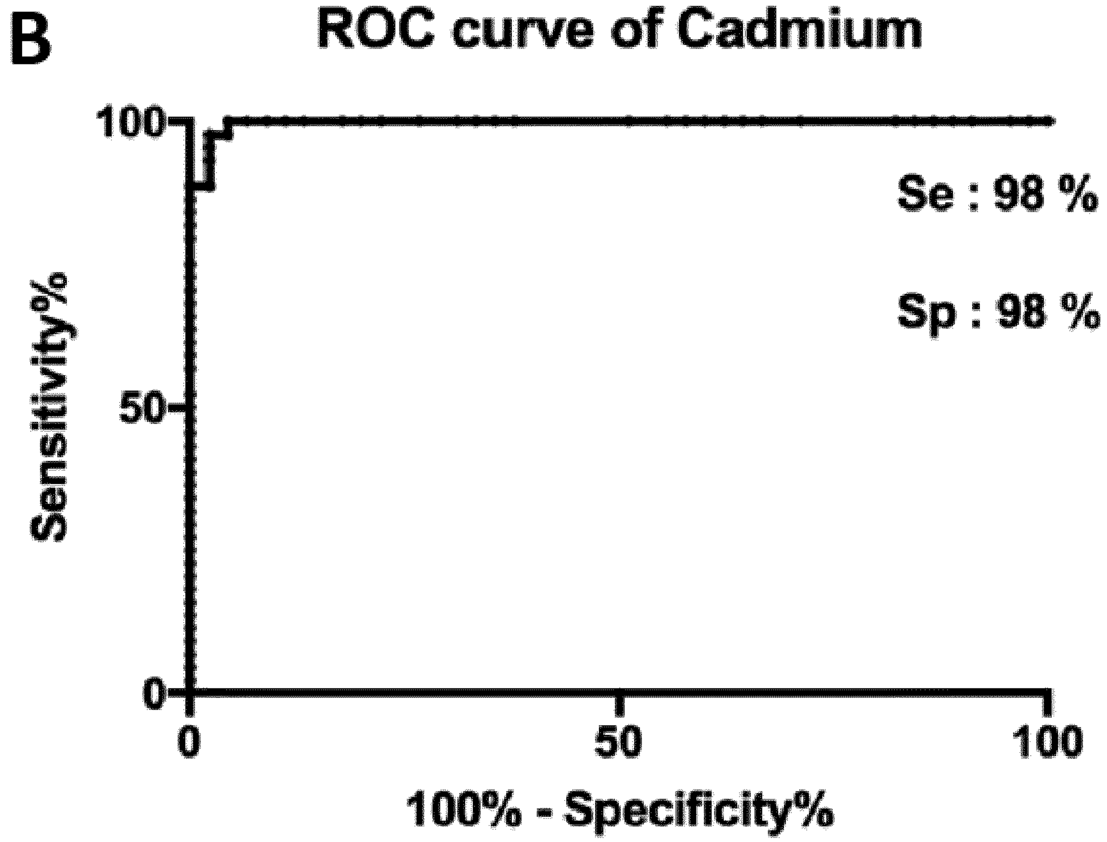
Figure 7C:
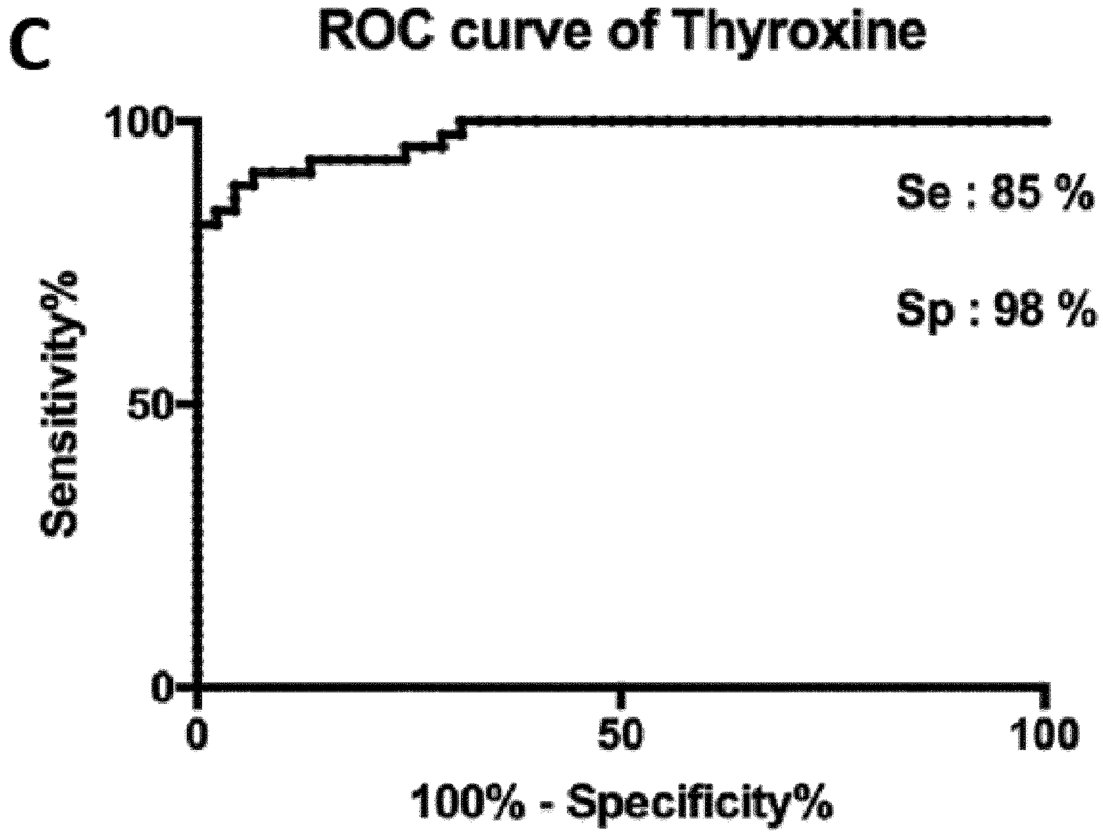
Figure 7D:
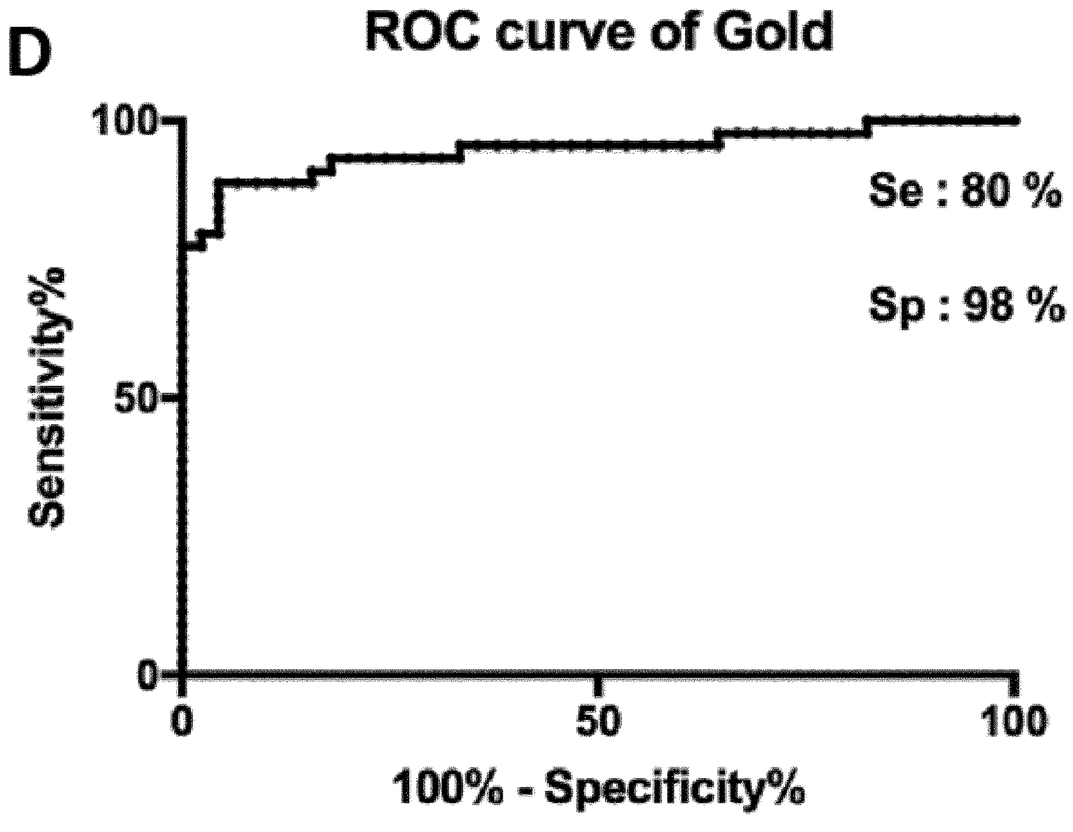
Figure 7E:
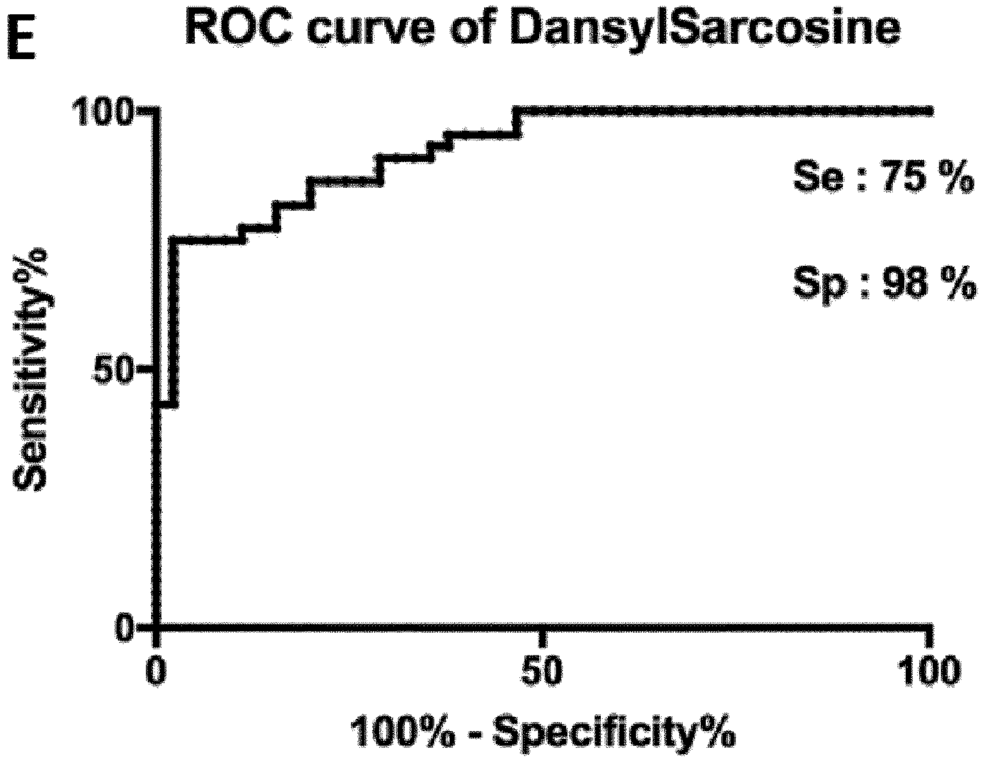

FIG. 6. (A-D) Relative abundances of albumin isoforms in all the groups of rats. Alb-Acet, Alb-Cys, Alb-Gly, and Alb-Glut stands for acetylated albumin, cysteinylated albumin, glycosylated albumin and glutathione-conjugated albumin respectively. *=$p<0.05$; ** $p<0.01$.

FIG. 7. (A-E) Discrimination between control patients with no liver disease and cirrhotic patients by SEB test in the development cohort.

Figure 8:
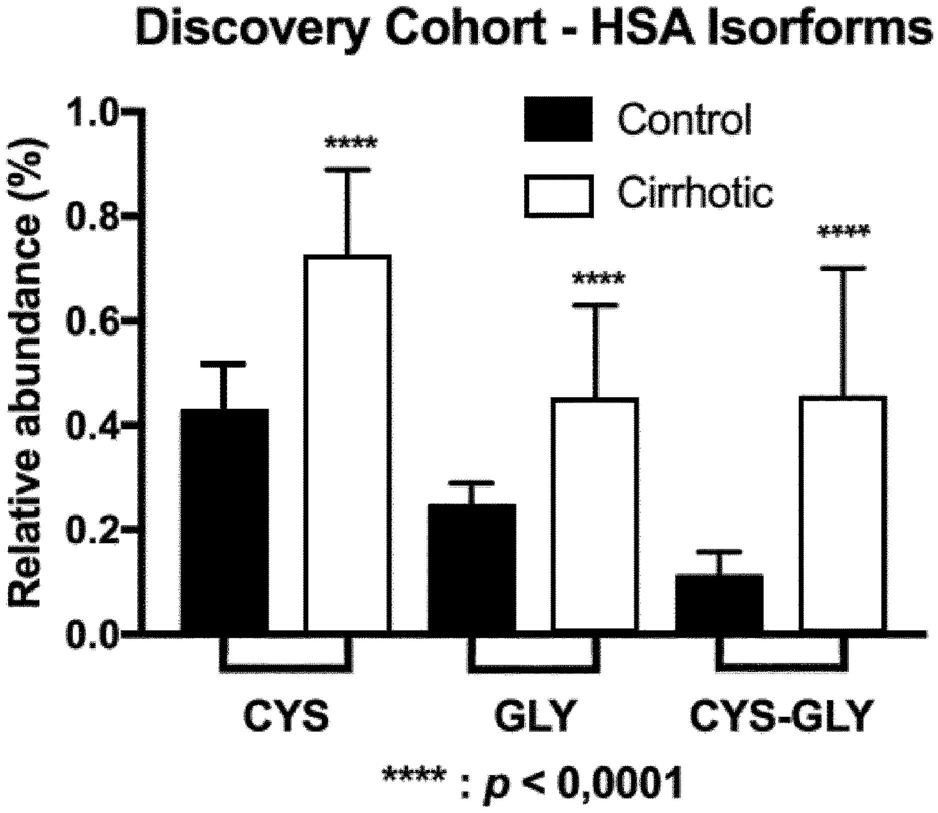

FIG. 8. Determination of the 3 most abundant HSA isoforms in 45 cirrhotic and 45 control patients.

EXAMPLE: THE "SERUM ENHANCED BINDING" TEST AS A BIOMARKER OF LIVER DYSFUNCTION

Methods

Chemicals:

The following reagents were purchased form Sigma-Aldrich and used to prepare the ligands solutions: cobalt(II) chloride (CAS: 7646-79-9), gold(III) chloride trihydrate (CAS: 16961-25-4), copper(II) chloride (CAS: 7447-39-4), silver acetate (CAS: 563-63-3), L-thyroxine sodium salt pentahydrate (CAS: 6106-07-6). Dansylsarcosine Piperidinium Salt >95%, was purchased from RareChemicals GmbH. All ligands solutions were prepared in MiliQ purified water. Albumin Vialebex®, 200 mg/mL was used to test HSA binding capacity.

Patients and Samples

Patient samples were all from blood leftovers of biochemistry laboratory tests prescribed according to the standard of care. In accordance with French regulations and Good Clinical Practice for biomedical studies, patients were informed of, and were able to oppose to, the use of the leftovers of their blood samples at any time (CSP article L1211-2). The cohort was composed of cirrhotic patients and of patients with no liver dysfunction as controls. Patients were considered as free from liver dysfunction on the basis of their clinical diagnosis and their liver function biochemical tests, namely, aspartate transaminase, alanine transaminase, alkaline phosphatase, γ-glutamyltransferase, free and total bilirubin and albumin.

Cirrhotic patients were included based on the gastroenterologists' diagnosis, their liver function biochemical tests and their Child-Pugh scores.

Plasmas or serums were obtained by centrifugation of blood at 3000 rpm for 10 min at 4° C. For the cohort, the SEB test was performed within 24 h of the biochemical tests. When volume permitted, plasma or serum samples were then stored at −20° C. for stability tests.

HSA isoforms were determined for all patients, as described below.

Study of the Binding Capacities of HAS in Patients with No Hepatic Dysfunction:

In a first step, we have evaluated separately the global capacity of serum to bind Cu, Au, L-thyroxine, Cd and dansylsarcosine in patients with no liver dysfunctions. Increasing concentrations of each ligand were added to patient serum samples in order to obtain HSA/ligand theoretical ratios (mol/mol) of 1/1, 1/5, 1/10, 1/20, 1/50, 1/100, 1/500 and 1/1000 when possible. These theoretical ratios were calculated on the basis of HSA blood concentration of 0.6 mM, which is an average concentration in healthy subjects.

Six different serums (from six different patients) per ratio and per ligand were used for this evaluation. After incubation for 30 min of the serum samples spiked with a ligand, they were ultracentrifugated to measure the unbound ligand in the ultrafiltrates. In details, Serum (200 μL) was incubated for 30 min at 4° C. with the abovementioned ligands with different solutions concentrations (500 μL of solutions at increasing concentrations of ligands), The incubated serum was ultrafiltrated on Amicon® filters with a 30 kDa cut-off, The ultrafiltrate (10 μL) was then diluted in $HNO_3$ 0.1 M before analysis using a multi-element ICP-MS method for the determination of free (unbound) ligand concentrations. The ICP-MS method measured Cu, Au, Cd, iodine (for L-Thyroxine) and sulfur (for dansylsarcosine) separately or simultaneously, depending on the sample content.

Percentages of retained ligands quantity as well as the real ratios of HSA/bound ligands (mol/mol) were then calculated, since the actual HSA concentration in each serum was known.

This allowed us to determine the maximum capacity of the serum to bind each ligand. These ceilings are at the basis of the SEB test to discriminate serum with modified HSA forms from serum with mostly native HSA.

Comparison of Binding Capacities of HSA in Cirrhotic Patients and Controls (Patients Without Hepatic Dysfunction)

Discovery Cohort

After setting thresholds corresponding to the retention of more than 90% of each ligand, we performed the SEB test on the serum of patients with diagnosed cirrhosis (n=18) as compared to patients with no liver dysfunctions (n=18). The SEB test was then performed as described above but with the different solutions containing ligands, at specific concentrations proportional to the ligands' binding threshold. Briefly, solutions of Cu, Au, dansylsarcosine and L-thyroxine were prepared at 5950 μM, 23800 μM, 11900 μM and 150 μM, respectively. The solutions were incubated separately with 200 μL of serum for Cu, Au, and dansylsarcosine and with 50 μL of serum for L-thyroxine.

Albumin isoforms were determined in all serum samples of these two groups as described below.

In another experiment, we analyzed serum samples from 12 cirrhotic patients and 12 controls in order to study the discrimination power of the test when using solutions of ligands at lower concentrations. For this, Cu, Cd and Au solutions concentrations were set at 1190 μM for Cu, 1190 μM for Cd, 11900 μM for Au and 75 for L-thyroxine 75 μM.

Development Cohorts

The SEB test and the identification of the most important isoforms of HSA, namely, HSA-Cys, HAS-Gly and HAS-Cys-Gly, were performed as described previously in a development cohort including 45 cirrhotic patients and 45 patients with no liver impairments. The statistical analysis were performed to discriminate patients in a first step then to discriminate patients upon their Child-Pugh scores (Class A (CA): "least severe liver disease", Class B (CB): "moderately severe liver disease", Class C (CC): "most severe liver disease"). The dataset was split up in a training (75%) and a testing (25%) dataset using random table. Prediction models were developed using extreme gradient boosting (package R xgboost v0.90.0.2) including 2 repetitions of 3 groups cross validations for isoform alone or for ligands of SEB test alone. Global discrimination capacity of disease vs non disease and discrimination for each Child-Pugh stage of cirrhosis were tested. The performances were evaluated in the testing data and the confusion matrix was drawn as well as global accuracy and its 95% CI.

Animal Model:

We also set up an animal experiment to investigate the time and severity of liver dysfunction at which the test turns positive. In this experimentation, high doses of ethanol were used to induce liver injuries in six groups of male Wistar rats (Janvier Labs, France). Each group contained 6 to 9 rats. Two ml of a solution of 50% of ethanol (0.4 g of ethanol) was administrated orally for 1 day in the $1^{st}$ group, for 3 days in the $2^{nd}$ group, for 7 days in the $3^{rd}$, for 10 days in the $4^{th}$ group and for 14 days in the $5^{th}$ group. Blood and liver were collected from the sacrificed rats 24 h after the last ethanol administration. A control group (n=9) received oral administration or a saline solution for 14 days and rats were sacrificed and sampled at day 15. The SEB test was applied to the rats of all these groups. Albumin isoforms, as described below, were also determined for all the groups.

ICP-MS analysis

Calibration curves were built with 6 calibrants for each element. Concentrations ranged between 10 and 100 μg/L for Cu, Cd, Au and sulfur and between 1 and 20 μg/L for L-thyroxine.

L-cystein was used for the calibration of sulfur and L-thyroxine for the calibration of iodine. Cu was measured Cu at m/z 65, Cd at m/z 112, Au at m/z 197, iodine at m/z 127 and sulfur at m/z 48 as described in EL BALKHI et al. 2010 [9]. To be able to measure sulfur ($^{32}S$), interfered by $^{32}O_2$, we introduced oxygen as a reactant gas in the reaction cell of the instrument to generate $^{48}SO$. For this, the kinetic energy discrimination (KED) mode was used with oxygen flow rate at 0.3 ml/min. This was applied for all element measurements and for all calibration points, controls and ultrafiltrates. The ultrafiltrates were diluted with $HNO_3$ 0.1 M when necessary.

HSA Isoforms Determinations:

To study the albumin modifications in all samples, analysis was carried out using micro-liquid chromatography coupled to high resolution Q-TOF mass spectrometry (TripleTOF® 5600+, Sciex). Plasma or serum samples from all studied groups were diluted with ultrapure water to 1:1,000 (v:v) and 5 μL of the diluted serum were injected. A C4 Chrom XP (100×0.3 mm; 3 μm) Eksigent column was used for the chromatographic separation of albumin isoforms, together with a mobile phase solvent A (0.1% formic acid in ultrapure water) and solvent B (0.1% formic acid in acetonitrile). The analysis was performed in gradient mode, programmed as follows: 0-1 min, 20% B; 1-5 min, 20% to 50% B; 5-6 min, 50% to 95% B; 6-8 min, 95% B; 8-8.5 min; 95% to 20% B; 8.5-13 min, equilibration with 20% B. The run lasted 13 min and the total flow rate was kept constant at 5 μL/min.

All MS parameters were controlled by Analyst® TF 1.7 (Sciex). m/z ratios were first scanned from m/z 400 and 1250 using the TOF MS scan mode with an accumulation time of 2 s. The albumin spectra obtained were then deconvoluted within the mass range from 66,000 Da to 67,000 Da with PeakView 2.1 software (Sciex). From the intensity of the peak, the relative abundance of albumin isoforms was calculated relative to the intensity of native albumin.

The same method of isoform determination was applied to rat serum obtained from the animal experiment.

Results

Enhanced Binding Capacity of Serum/HSA

By adding increasing concentrations of Cu to serum, we observed that up to 12 Cu atoms per albumin molecule were retained on the ultracentrifugation filter with an average retention of 95%. This percentage dropped to 40% or less when more Cu was added (FIG. 1A to 1D). Serum samples were able to bind with 100% retention up to 150 atoms of Au, 50 atoms of Cd and 2.5 molecules of dansylsarcosine per molecule of albumin. Serum samples were able to bind at least 10 molecules of L-thyroxine with 100% retention, but L-thyroxine could not be tested above the 1/10 ratio (HSA/L-thyroxine) because of dissolution problems. In order to confirm that the binding is only due to HAS and that there is no unspecific binding to other serum proteins, we performed the same tests with the Vialebex® commercial albumin solution at 200 mg/mL (supplemental data). The binding capacities of commercial solution of pure HSA were equivalent or higher than those of patient serum: for instance, the Cu/HSA retention ratio was 40 and the Au/HSA 150.

Based on these results we set thresholds best able to discriminate native HSA from modified HSA. Solutions of Au, Cu, dansylsarcosine and L-thyroxine were then prepared to obtain theoretical ratios of 1/100, 1/10, 1/5, and 1/10, respectively. The solutions were then incubated with serums samples from cirrhotic and control patients, as described above.

Comparison of Serum Enhanced Binding Capacities in Cirrhotic and Patients with No Liver Dysfunction Discovery Cohort Among the 18 cirrhotic patients, cirrhosis was due to alcohol alone in 8 patients, to alcohol and VHC in 1 case, to a metabolic syndrome (NASH) in 5 cases, alcohol and NASH in 3 cases, alcohol, NASH and viral infection in 1 case. Albumin concentrations ranged between 18.2 and 34 g/L. Child-Pugh scores for all patients are shown in Table 1.

Au, dansylcarcosine, and L-thyroxine were able to discriminate with 100% specificity and sensitivity cirrhotic patients from control patients, as shown in FIG. 2A to 2D. Cu was able to discriminate cirrhotic patients with 72% specificity but with 100% sensitivity.

All the 18 cirrhotic patients and the 18 control patients were analyzed to determine the abundance of HSA isoforms in their serum. We observed high abundances of HSA isoforms in all cirrhotic patients with the presence of significantly increased cysteinylated HSA (HSA-Cys), Glycated HSA (HSA-Gly), nitrosylated HSA (HSA-NO3) and cysteinylated and nitrosylated HSA (HSA-Cys/NO3), as shown in FIG. 3.

In a second step, 12 cirrhotic patients and 12 control patients were then included to test lower concentrations for Cu, Au and L-thyroxine (1/5, 1/50 and 1/5, respectively). Additionally, Cd was tested in this group at a ratio of HSA/Cd of 1/5. All the ligands were able to discriminate cirrhotic patients with 100% sensitivity and specificity as shown in FIG. 4A to 4D.

Development Cohort

As shown in FIG. 7A to 7E, the performances of the SEB test ligands were consistent with the previous results: the specificity and sensitivity of Cu and Cd were 98%; L-thyroxine offered Se 85% and Sp 98%; Au Se and Sp were 80 and 98%. However, dansylsarcosine Se and Sp were only of 75% and 98%, respectively. When all the ligands were taken together in a principal component analysis, the group of cirrhotic patients was visibly well separated from control patients (data not shown). The 3 principal HSA isoforms were significantly higher in cirrhotic patients in comparison with control patients as shown in FIG. 8.

The cohort included 45 cirrhotic patients and 45 patients with no liver dysfunctions. Among the 45 cirrhotic patients, 6 were removed due to absence of formal classification of the disease but these patients were used to be predicted by the final models. So the training set included 65 patients (12CA, 11CB, 6CC and 36 N) and the testing 19 patients (3 CA, 3 CB, 1 CC and 12 N).

Uniclass Model for SEB Test Ligands: Cirrhosis Vs No Cirrhosis

The parameters of the best model for "ligands uniclass" were nrounds=5 (number of passes on the data), max_depth=2 (Maximum depth of a tree), eta=0.3 (learning rate), colsample_bytree=0.25 (is the subsample ratio of columns when constructing each tree), subsample=0.5 (Subsample ratio of the training instances).

Performance in the testing dataset were excellent with an accuracy (CI95%)=1 (0.82, 1). Seven cirrhotic patients and 12 patients with no liver dysfunctions were well predicted with no false positive or false negative.

Uniclass Model for HSA Isoform: Cirrhosis Vs No Cirrhosis

The parameters of the best model for "metals uniclass" were nrounds=5 (number of passes on the data), max_depth=2 (Maximum depth of a tree), eta=0.3 (learning rate), colsample_bytree=0.25 (is the subsample ratio of columns when constructing each tree), subsample=0.5 (Subsample ratio of the training instances).

Performance in the testing dataset were excellent with an accuracy (CI95%)=0.95 (0.74, 0.999). Among the 12 patients with no liver impairments, 12 were well predicted and only one cirrhotic patient was not well predicted.

Multiclass Model for SEB Test Ligands

The parameters of the best model for "metals multiclass" were nrounds=5 (number of passes on the data), max_depth=2 (Maximum depth of a tree), eta=0.2 (learning rate), colsample_bytree=0.5 (is the subsample ratio of columns when constructing each tree), subsample=1 (Subsample ratio of the training instances).

Performance in the testing dataset offered an accuracy (CI95%)=0.79 (0.54, 0.94). The confusion matrix was as follows:

| | Reference | | | |
|---|---|---|---|---|
| Prediction | CA | CB | CC | N |
| CA | 1 | 1 | 1 | 0 |
| CB | 2 | 2 | 0 | 0 |
| CC | 0 | 0 | 0 | 0 |
| N | 0 | 0 | 0 | 12 |

Model for Isoform Multiclass: Prediction of Child-Pugh Scores

The parameters of the best model for "isoforms multiclass" were nrounds=5 (number of passes on the data), max_depth=2 (Maximum depth of a tree), eta=0.1 (learning rate), colsample_bytree=1 (is the subsample ratio of columns when constructing each tree), subsample=1 (Subsample ratio of the training instances).

Performance of HSA isoforms in the testing dataset showed an accuracy (CI95%)=0.84 (0.60, 0.97). Three cirrhotic patients out of 7 were not well predicted.

Animal Experiment

After daily administration of 0.4 g of ethanol (1.6 g ethanol/kg of body weight) to the different groups of rats, we observed a significant increase of AST in the groups receiving ethanol for more than 7 days. After 10 days of ethanol administrations ALT was significantly higher than in the control group. Alkaline phosphatase (ALP), free and total bilirubin were unchanged in comparison to controls (Table 2). Histological tests on the liver of rats of group D14 showed a very slight fibrosis (data not shown). No liver tissue damages were visible in the other groups.

The SEB test was performed in the serum of all groups of rats using Cu, Cd, L-thyroxine at thresholds 1/5 and Au at a threshold 1/50, as described above. As shown in FIG. 5A to 5D, all rats in the group D14 were positive for all tested ligands. Rat serum had decreasing binding capacities for Au after the first day of administration but this capacity was restored in the group D7. The same profile was observed for the biding capacity of Cu and L-thyroxine. However, the binding capacity of Cd was only decreased in the group D14.

Micro-LC—HRMS showed significant increases of all the identified albumin isoforms in these groups of rats. As depicted in FIG. 6A to 6D, acetylated albumin (Alb-Acet), glycosylated albumin (Alb-Gly), and gluthation-conjugated albumin increased very rapidly showing significant differences between groups. The cysteinylated albumin (Alb-Cys) was increased also in all groups, except D7.

Discussion

In this study, we have demonstrated that the binding capacities of the selected ligands are significantly different between cirrhotic patients and patients with no liver dysfunctions. The decreased binding capacities in cirrhotic patients were paralleled by the presence of significantly higher HSA isoforms. This allow us to assume that the most important modifications of albumin structure due to liver dysfunction could be revealed by measuring the unbound fraction of specific ligands spiked in serum. Several studies have reported HSA chemical and/or structural modifications in advanced liver diseases.

Albumin chemical modifications have been extensively reviewed in [7, 10]. Albumin undergoes several post-translational modifications including: acetylation, cysteinylation, homocysteinylation, glutathionylation, glycosylation, glycation, nitrosylation, nitration, phosphorylation and oxidation.

Although oxidation could affect several residues such as methionine, lysine, arginine, and proline, the oxidation of the Cys34 residue is the most studied. This modification was characterized on the basis of the redox state of Cys34 as follows:

1. Human mercaptalbumin (HMA), the reduced and most abundant form of HAS (70-80% of total HAS in healthy subjects),
2. Nonmercaptalbumin 1 (HNA1), a reversibly oxidized form (20-30%) and
3. Nonmercaptalbumin 2 (HNA2) the irreversible oxidized form of albumin (<5%)[10].

The clinical relevance of these modifications has been recently investigated in advanced liver diseases (1-4,11,12) [1-4, 11, 12]. The significant reductions in HMA percentage with a concomitant increase in HNA1 and HNA2 isoforms have been well documented in end-stage liver injuries. It has also been reported that a progressive increase of the oxidized forms of HSA is detected in cirrhotic patients. In particular, circulating levels of both HNA1 and HNA2 were increased in patients with decompensated cirrhosis and, to a greater extent, in those with acute-on-chronic liver failure, a syndrome characterized by a very high short-term mortality rate [2, 4, 7]. Interestingly, in these patients, HNA2 level significantly correlated with parameters of systemic inflammation and was directly related to disease prognosis. Lately, it was reported that patients with severe alcoholic hepatitis (SAH) had a significant increase in albumin oxidation due to the oxidative stress environment related to the disease. In such conditions, albumin acts as a pro-oxidant and promotes additional oxidative stress and inflammation through activation of neutrophils [13]. Of note, in this study, HNA2 was only increased in SAH and not in chronic alcoholic cirrhotic patients.

Structural alterations involving sites other than Cys34 were also reported. N- or C-terminal truncated, as well as glycated, forms were found in plasma samples from patients with acutely decompensated cirrhosis or severe alcoholic hepatitis [14]. Dimerization of HSA has also been reported in patients with decompensated cirrhosis, although a controversy exists about its pejorative role in the disease. However, the homodimeric isoform with N-terminal truncation was independently associated to disease complications and was able to stratify 1-year survival [14]. Very recently, it has been reported that in SAH patients, excess binding of bilirubin with albumin helps to predict 3-months mortality and that this excessive binding contributes to the observed decrease in binding capacity of dansylsarcosine to albumin [15].

Therefore, to elaborate the SEB test, we have selected several ligands with known specific binding sites on albumin. The binding sites were chosen in order to cover the most important HSA modifications with reported clinical relevance in liver dysfunctions. On these bases, Au was selected to reveal Cys34 modifications (16-18)[16-18], Cu for its high affinity to the N-terminal site and the multi binding site B [18, 19], L-thyroxine for its 4 binding sites distributed in the 4 cavities of HSA (Tr1 to Tr4) [20], dansylsarconsine for its affinity to the drug site 3 (or diazepam-binding site), which is also the bilirubin binding site [5], and Cd for its high affinity to the multi binding sites A (or Cd binding site) [8].

We observed that serum is able to bind up to 12 atoms of Cu, 150 atoms of Au, 50 atoms of Cd, 2.5 molecules of dansylsarcosine and at least 10 molecules of L-thyroxine per molecule of albumin. These values were much higher than the theoretical and experimental reported ones. For instance, it has been reported that HSA is able to bind less than 2 atoms of Cu [21]. It has been confirmed later that only one specific binding site, namely, the NTS is able to bind Cu, and that the multi metal binding site has a very low affinity for Cu. In this kind of studies, metal binding strategies employing equilibrium dialysis were mostly used [22, 23]. In the later studies, low molecular weight weak chelates were used to prevent metal hydrolysis and subsequent polymerization and thus nonspecific binding. In our experimental conditions in the SEB test, metals hydrolysis could obviously occur which could be responsible for nonspecific bindings due to Van der Waals forces [23]. These nonspecific bindings are even more important when commercial and pure solutions of HSA are incubated with our ligands (supplemental data). The presence of endogenous weak chelators (such as free amino acids) in serum could be the reason behind this. In an in silico model we were able to demonstrate that HSA is able to bind covalently 2 atoms of copper in 2 specific binding sites and up to 40 atoms of copper at different non specific binding sites (Data not shown). Therefore, we decided to apply the SEB test with lower ligands concentrations. All the tested ligands were then able to discriminate cirrhotic patients from non-cirrhotic individuals with 100% sensitivity and 100% specificity in the discovery cohort. The performance of the SEB test was excellent in the development cohort.

The nature and relative abundances of the HSA isoforms found in our analysis are in agreement with previous results [2, 4, 12, 13, 15] and with the results of the SEB test. Indeed, in comparison with patients with normal liver functions, all the cirrhotic patients presented high levels of modified HSA (nitrosylation, cysteinylation and glycation). Nitrosylation and cysteinylation occur on the Cys34 [1], which is consistent with decreased Au binding to HSA in cirrhotic patients. Glycation can occur on Lys199, Lys281, Lys439, and Lys525 [3], all located near the L-thyroxine sites, which might hinder this ligand to bind to HSA. Finally, it has been demonstrated that oxidation of Cys34 could result in a number of conformational changes of HSA [5]. It alters the conformation and dynamics of the entire domain I, as well as of the domain I/II interface, which results in lower binding capacities of endogenous (L-Trp) and exogenous ligands (cefazoline and verapamil), whose binding sites are distant from cys34. This point could explain the decreasing binding capacity of Cd in cirrhotic patients. Cd is reported to coordinate with one His and four carboxylates; however, its location is unknown but should be distant from Cys34 [23].

Despite the very small patient numbers, we observed that the binding capacity of HSA is more decreased in alcohol cirrhotic patients that in those with metabolic cirrhosis or in mixed cirrhosis (Table 1). The HSA-Cys isoform seems to be higher in the first group. The same observation could be done with the results of the Cu SEB test. In addition, patients with the highest Child and MELD scores (patients 2,3 and 8) have the highest HSA-Cys abundances. Patient 19 (not included in the statistics) had a NASH without cirrhosis. The abundance of his HSA-Cys is among the lowest but L-thyroxine and Au binding to HAS was lower than in control patients and higher than in cirrhotic patients. This might be explained by the modifications of Cys34 and L-thyroxine sites and the absence of modification in the NTS, but we have no clue to support this hypothesis so far.

The animal model allowed us to demonstrate that the albumin modifications were mostly acetylation, cysteinylation, glycation and glutathionylation. The SEB test was positive for Cd at Day 14, and for Au and L-thyroxine as soon as D1. Liver injuries after D7 were confirmed by increased serum concentrations of AST and ALT, markers of hepatocyte integrity. As the albumin of rats has not been crystalized and its 3D structure elucidated yet, it is hard to find the link between albumin modifications and binding capacities. However, the results suggest that our test may reveal hepatocyte suffering early, before the current biochemistry biomarkers and that decreased capacity of albumin to bind Cd could be a marker of more advanced liver injuries.

TABLES

TABLE 1

Patients age and etiology of cirrhosis are indicated along with their Child-Pugh and MELD scores. The abundances of identified albumin isoforms were all higher than in control patients. Isoform percentages are calculated on the basis of the abundance of the native HSA. For all the tested patients the SEB test was positive in comparison to control patients except for Cu in some patients. Ratios are calculated as follows: concentration of ligands in the filtrates (μM)/concentration of albumin (μg/L).

| Patient | Age | Cirrhosis etiology | MELD Score | Child-Pugh Score | HSA Cys (%) | HSA Gly (%) | HSA NO3 (%) | HSA Cys-NO3 (%) | Ratio Au/HSA | Ratio Cu/HSA | Ratio LT/HSA | Ratio DS/HSA |
|---|---|---|---|---|---|---|---|---|---|---|---|---|
| | | Reference values in Control patients (mean +/− SD) | | | 0.63 +/− 0.11 | 0.39 +/− 0.04 | 0.48 +/− 0.02 | 0.42 +/− 0.06 | 10 +/− 7.9 | 4.3 +/− 1.6 | 0.09 +/− 0.03 | 0.23 +/− 0.26 |
| 1 | 64 | Alcohol | n.a | B | 1.25 | 0.71 | 0.54 | 0.76 | 86.23 | 7.5 | 1.82 | n.a |
| 2 | 74 | | 23 | C14 | 1.16 | 0.57 | 0.57 | 0.73 | 57.8 | 4.97 | 0.86 | n.a |
| 3 | 69 | | 23 | C | 1.84 | 0.81 | 0.63 | 1.21 | 120.09 | 9.33 | 3.04 | n.a |
| 4 | 47 | | 9 | B9 | 0.79 | 0.41 | 0.49 | 0.44 | 102.89 | 15.85 | 1.4 | n.a |
| 5 | 52 | | 15 | C12 | 0.77 | 0.53 | 0.58 | 0.61 | n.a | 5.5 | n.a | n.a |
| 6 | 73 | | 16 | B8 | 1 | 0.45 | 0.47 | 0.6 | 145.77 | 10.45 | 3.33 | 4.77 |
| 7 | 70 | | 14 | C10 | 0.83 | 0.54 | 0.49 | 0.5 | 84.18 | 9.07 | 2.71 | 2.26 |
| 8 | 72 | | 24 | C11 | 1.24 | 0.61 | 0.55 | 0.74 | 89.43 | 6.86 | 2.17 | 5.71 |
| 9 | 80 | NASH | 21 | B9 | 0.9 | 0.53 | 0.53 | 0.64 | n.a | 9.64 | n.a | n.a |
| 10 | 70 | | n.a | n.a | 0.89 | 0.61 | 0.62 | 0.73 | n.a | 7.54 | n.a | n.a |
| 11 | 77 | | n.a | n.a | 0.83 | 0.6 | 0.52 | 0.55 | 61.55 | 6.74 | 2.06 | 7.58 |
| 12 | 77 | | n.a | A | 0.82 | 0.38 | 0.44 | 0.47 | 46.25 | 4.76 | 1.92 | 0.78 |
| 13 | 75 | | 7 | n.a | 0.88 | 0.46 | 0.54 | 0.61 | 64.58 | 5.59 | 1.72 | n.a |
| 14 | 80 | Mixt: alcohol and | 7 | A5 | 0.66 | 0.46 | 0.49 | 0.45 | 97.75 | 8.25 | 2.15 | n.a |
| 15 | 80 | NASH | 29 | B9 | 1.69 | 0.63 | 0.59 | 1.05 | 116.64 | 10.68 | 2.52 | n.a |
| 16 | 78 | | 7 | A6 | 0.73 | 0.39 | 0.47 | 0.45 | 87.56 | 11.02 | 2.55 | 16.38 |
| 17 | 62 | Mixt: alcohol and VHC | 12 | B9 | 0.89 | 0.54 | 0.52 | 0.59 | 39.78 | 5.26 | 1.52 | n.a |
| 18 | 50 | Mixt: VHC, alcohol and NASH | 15 | C | 1.05 | 0.51 | 0.51 | 0.67 | 70.47 | 5.56 | 1.24 | n.a |
| 19 | 60 | NASH without cirrhosis | n.a | n.a | 0.73 | 0.35 | 0.45 | 0.41 | 59.64 | 5.1 | 1.9 | n.a |

TABLE 2

Biochemical test results in rats after daily administration of ethanol for different time spans. Group D 1 received ethanol for 1 day, D 3 for 3 days, D 7 for 7 days, D 10 for 10 days and D 14 for 14 days.

| Tests | Control rats | Group D 1 | Group D 3 | Group D 7 | Group D 10 | Group D 14 |
|---|---|---|---|---|---|---|
| ALB (g/L) | 14.4 [12.7-17.6] | 13.8 [13.2-14.1] | 12.4* [11.8-14.2] | 12.2* [11.0-13.8] | 16.35 [12.4-17.7] | 12.9* [10.2-13.5] |
| AST (UI/L) | 70.8 [61-75] | 78 [70-85] | 80 [52-144] | 96* [75-157] | 92* [81-157] | 90* [85-294] |
| ALT (UI/L) | 57 [46-61] | 63 [52-71] | 62 [46-123] | 69 [52-97] | 78* [68-98] | 82* [65-104] |
| ALP (UI/L) | 196 [101-325] | 232 [153-304] | 180 [121-329] | 159 [84-263] | 172 [100-222] | 230 [110-327] |
| Free BILI (μM) | 0.75 [0.6-1] | 0.7 [0.3-1] | 0.7 [0.5-1.3] | 0.7 [0.4-4.4] | 0.8 [0.5-1.1] | 0.6 [0.4-0.7] |
| Total BILI (μM) | 0.75 [0.4-1.3] | 0.8 [0.4-1.6] | 0.8 [0.2-1.7] | 1 [0.2-1.9] | 1 [0.8-1.6] | 0.9 [0.5-1.8] |

REFERENCES

Throughout this application, various references describe the state of the art to which this invention pertains. The disclosures of these references are hereby incorporated by reference into the present disclosure.

1. Naldi M, Baldassarre M, Domenicali M, et al (2017) Structural and functional integrity of human serum albumin: Analytical approaches and clinical relevance in patients with liver cirrhosis. J Pharm Biomed Anal 144: 138-153. doi: 10.1016/j.jpba.2017.04.023
2. Domenicali M, Baldassarre M, Giannone F A, et al (2014) Posttranscriptional changes of serum albumin: clinical and prognostic significance in hospitalized patients with cirrhosis. Hepatol Baltim Md 60:1851-1860. doi: 10.1002/hep.27322
3. Naldi M, Baldassarre M, Domenicali M, et al (2016) Mass spectrometry characterization of circulating human serum albumin microheterogeneity in patients with alcoholic hepatitis. J Pharm Biomed Anal 122:141-147. doi: 10.1016/j.jpba.2016.01.048
4. Oettl K, Birner-Gruenberger R, Spindelboeck W, et al (2013) Oxidative albumin damage in chronic liver failure: relation to albumin binding capacity, liver dysfunction and survival. J Hepatol 59:978-983. doi: 10.1016/j.jhep.2013.06.013
5. Kawakami A, Kubota K, Yamada N, et al (2006) Identification and characterization of oxidized human serum albumin. A slight structural change impairs its ligand-binding and antioxidant functions. FEBS J 273:3346-3357. doi: 10.1111/j.1742-4658.2006.05341.x
6. Bar-Or D, Lau E, Winkler J V (2000) A novel assay for cobalt-albumin binding and its potential as a marker for myocardial ischemia-a preliminary report. J Emerg Med 19:311-315
7. Klammt S, Mitzner S, Stange J, et al (2007) Albumin-binding function is reduced in patients with decompensated cirrhosis and correlates inversely with severity of liver disease assessed by model for end-stage liver disease. Eur J Gastroenterol Hepatol 19:257-263. doi: 10.1097/MEG.0b013e3280101f7d
8. Fanali G, di Masi A, Trezza V, et al (2012) Human serum albumin: from bench to bedside. Mol Aspects Med 33:209-290. doi: 10.1016/j.mam.2011.12.002
9. El Balkhi S, Poupon J, Trocello J-M, et al (2010) Human plasma copper proteins speciation by size exclusion chromatography coupled to inductively coupled plasma mass spectrometry. Solutions for columns calibration by sulfur detection. Anal Chem 82:6904-6910. doi: 10.1021/ac101128x
10. Bonneau E, Tétreault N, Robitaille R, et al (2016) Metabolomics: Perspectives on potential biomarkers in organ transplantation and immunosuppressant toxicity. Clin Biochem 49:377-384. doi: 10.1016/j.clinbiochem.2016.01.006
11. Spinella R, Sawhney R, Jalan R (2016) Albumin in chronic liver disease: structure, functions and therapeutic implications. Hepatol Int 10:124-132. doi: 10.1007/s12072-015-9665-6
12. Stauber R E, Spindelboeck W, Haas J, et al (2014) Human nonmercaptalbumin-2: a novel prognostic marker in chronic liver failure. Ther Apher Dial Off Peer-Rev J Int Soc Apher Jpn Soc Apher Jpn Soc Dial Ther 18:74-78. doi: 10.1111/1744-9987.12024
13. Das S, Maras J S, Hussain M S, et al (2017) Hyperoxidized albumin modulates neutrophils to induce oxidative stress and inflammation in severe alcoholic hepatitis. Hepatol Baltim Md 65:631-646. doi: 10.1002/hep.28897
14. Baldassarre M, Domenicali M, Naldi M, et al (2016) Albumin Homodimers in Patients with Cirrhosis: Clinical and Prognostic Relevance of a Novel Identified Structural Alteration of the Molecule. Sci Rep 6:35987. doi: 10.1038/srep35987
15. Das S, Maras J S, Maiwall R, et al (2018) Molecular Ellipticity of Circulating Albumin-Bilirubin Complex Associates With Mortality in Patients With Severe Alcoholic Hepatitis. Clin Gastroenterol Hepatol Off Clin Pract J Am Gastroenterol Assoc 16:1322-1332.e4. doi: 10.1016/j.cgh.2017.11.022
16. Li Y, Yan X-P, Chen C, et al (2007) Human serum albumin-mercurial species interactions. J Proteome Res 6:2277-2286. doi: 10.1021/pr0700403
17. Shen X-C, Liang H, Guo J-H, et al (2003) Studies on the interaction between Ag(+) and human serum albumin. J Inorg Biochem 95:124-130
18. Sokolowska M, Wszelaka-Rylik M, Poznański J, Bal W (2009) Spectroscopic and thermodynamic determination of three distinct binding sites for Co(II) ions in human serum albumin. J Inorg Biochem 103:1005-1013. doi: 10.1016/j.jinorgbio.2009.04.011
19. Peters T (1995) Ligand Binding by Albumin. In: All About Albumin. Elsevier, pp 76-132

20. Petitpas I, Petersen C E, Ha C-E, et al (2003) Structural basis of albumin-thyroxine interactions and familial dysalbuminemic hyperthyroxinemia. Proc Natl Acad Sci USA 100:6440-6445. doi: 10.1073/pnas.1137188100
21. Appleton D W, Sarkar B (1971) The Absence of Specific Copper(II)-binding Site in Dog Albumin A COMPARATIVE STUDY OF HUMAN AND DOG ALBUMINS. J Biol Chem 246:5040-5046
22. Masuoka J, Saltman P (1994) Zinc(II) and copper(II) binding to serum albumin. A comparative study of dog, bovine, and human albumin. J Biol Chem 269:25557-25561
23. Sendzik M, Pushie M J, Stefaniak E, Haas K L (2017) Structure and Affinity of Cu(I) Bound to Human Serum Albumin. Inorg Chem 56:15057-15065. doi: 10.1021/acs.inorgchem.7b02397

The invention claimed is:

1. A method for determining that a subject suffers or is at risk of suffering from a liver dysfunction, comprising the steps of obtaining a serum sample from the subject;

contacting a specific volume of the serum sample with specific concentrations of a plurality of ligands, wherein the specific concentration of each ligand achieves an optimal ratio of expected albumin present in the serum sample to ligand contacted with the sample, measuring in the serum sample a plurality of ligand binding capacities to serum albumin, wherein the plurality of ligand binding capacities is measured for L-thyroxine and one or more of gold (Au), copper (Cu), cadmium (Cd) and dansylsarcosine, wherein the specific concentrations of the plurality of ligands are expressed as a ratio of 1 molecule of albumin to X atoms or molecules of each ligand, wherein the ratio for Cu is in the range of 1/5 to 1/10, the ratio for L-thyroxine is in the range of 1/5 to 1/10, the ratio for Au is in the range of 1/50 to 1/100, the ratio for cadmium is 1/5 and the ratio for dansylsarcosine is 1/5;

determining that the subject suffers or is at risk of suffering from a liver dysfunction when the plurality of ligand binding capacities is decreased compared to the corresponding ligand binding capacities measured in serum of normal controls; and administering a suitable therapy to the subject, wherein the therapy is selected from the group consisting of a surgery to remove a gallbladder, an operation to treat portal hypertension and an immunosuppressive treatment.

2. The method of claim 1 wherein the subject suffers or is at risk of suffering from a liver disease selected from the group consisting of liver abscess, liver cancer, cirrhosis, amoebic liver abscess, autoimmune hepatitis, biliary atresia, coccidioidomycosis disseminated, portal hypertension, hepatic infections, hemochromatosis, pyogenic liver abscess, Reye's syndrome, sclerosing cholangitis, Wilson's disease, drug induced hepatotoxicity, fulminant liver failure and acute liver failure.

3. The method of claim 1 wherein the subject suffers from a non-alcoholic fatty liver disease.

4. The method of claim 1 wherein the subject underwent a liver transplantation.

5. The method of claim 1, further comprising the steps of contacting the specific volume of the serum sample with the specific concentrations of the plurality of ligands for a time sufficient for allowing the serum albumin to bind to the plurality of ligands, measuring the amounts of free ligands in the serum sample, and optionally calculating a ratio between the amounts of free ligands and the concentration of the serum albumin.

6. The method of claim 1 wherein binding capacity for 2, 3, 4 or 5 ligands is measured.

7. The method of claim 1 wherein the binding capacity is determined by mass spectrometry.

8. The method of claim 5 wherein a score which is a composite of the measured binding capacities is determined and compared to a reference value wherein a difference between said score and said reference value indicates whether the subject suffers or is at risk of suffering from a liver dysfunction.

9. The method of claim 8, wherein a classification algorithm is used to determine the score.

10. The method of claim 8, comprising the steps of a) measuring a plurality of binding capacities b) implementing a classification algorithm on data comprising the measured binding capacities so as to obtain an algorithm output; and c) determining the probability that the subject suffers from a liver dysfunction.

11. The method of claim 3, wherein the non-alcoholic fatty liver disease is non-alcoholic steatohepatitis (NASH).

12. The method of claim 7, wherein the mass spectrometry is inductively coupled plasma mass spectrometry (ICP-MS).

13. The method of claim 1, further comprising a step of identifying in the serum sample the presence of at least one human serum albumin (HSA) isoform associated with impaired ligand binding capacity selected from the group consisting of cysteinylated HSA (HSA-Cys), glycated HSA (HSA-Gly), nitrosylated HSA (HSA-NO3) and cysteinylated and nitrosylated HSA (HSA-Cys/NO3), following the measuring step.

14. A method of determining whether a subject suffers from a liver dysfunction and treating the subject, comprising obtaining a biological sample from the subject, wherein the biological sample is selected from the group consisting of blood and serum;

contacting a specific volume of the biological sample with specific concentrations of a plurality of ligands, wherein the specific concentration of each ligand achieves an optimal ratio of expected albumin present in the biological sample to ligand contacted with the sample, measuring, in the biological sample from the subject, a plurality of ligand binding capacities to serum albumin, wherein the plurality of ligand binding capacities is measured for gold (Au), copper (Cu), cadmium (Cd), L-thyroxine and dansylsarcosine, wherein the binding capacity is determined by mass spectrometry, wherein the specific concentrations of the plurality of ligands are expressed as a ratio of 1 molecule of albumin to X atoms or molecules of each ligand, wherein the ratio for Cu is in the range of 1/5 to 1/10, the ratio for L-thyroxine is in the range of 1/5 to 1/10, the ratio for Au is in the range of 1/50 to 1/100, the ratio for cadmium is 1/5 and the ratio for dansylsarcosine is 1/5; and wherein a difference between the plurality of ligand binding capacities and a corresponding predetermined reference value demonstrates an increase in albumin isoforms compared to the corresponding predetermined reference and indicates that the subject suffers or is at risk of suffering from the liver dysfunction, identifying in the biological sample the presence of at least one human serum albumin (HSA) isoform associated with impaired ligand binding capacity selected from the group consisting of cysteinylated HSA (HSA-Cys), glycated HSA (HSA-Gly), nitrosylated HSA (HSA-NO3) and cysteinylated and nitrosylated HSA (HSA-Cys/NO3); and treating the subject with a suitable therapy, wherein the therapy is selected from the group consisting of a surgery to remove a gallbladder, an operation to treat portal hypertension and an immunosuppressive treatment.

15. A method for identifying and treating a subject who suffers from or is at risk of suffering from a liver dysfunction, comprising the steps of obtaining a serum sample from the subject;

contacting a specific volume of the serum sample with specific concentrations of ligands consisting of gold (Au), copper (Cu), cadmium (Cd), L-thyroxine and dansylsarcosine, wherein the specific concentration of each of the ligands achieves a ratio of expected albumin present in the serum sample to ligand contacted with the sample, wherein the ratio for Cu is in the range of 1/5 to 1/10, the ratio for L-thyroxine is in the range of 1/5 to 1/10, the ratio for Au is in the range of 1/50 to 1/100, the ratio for cadmium is 1/5 and the ratio for dansylsarcosine is 1/5;

centrifuging and/or filtering at least one aliquot of the serum sample to separate a ligand-bound albumin fraction from a serum fraction of the serum sample;

measuring increased levels of free unbound ligand in the serum fraction for each of the ligands compared to corresponding free unbound ligands in serum fractions of serum samples from normal control subjects, wherein the serum samples from the normal control subjects have been subjected to the obtaining, contacting, and centrifuging and/or filtering steps to obtain the serum fraction from the normal control subjects;

identifying the subject tested as suffering from or at risk of suffering from a liver dysfunction; and administering a suitable therapy to the subject, wherein the therapy is selected from the group consisting of a surgery to remove a gallbladder, an operation to treat portal hypertension and an immunosuppressive treatment.

16. The method of claim 15, wherein the subject has undergone a liver transplant.

17. The method of claim 15, wherein the suitable therapy is an immunosuppressive treatment comprising administration of at least one drug or prodrug selected from the group consisting of azathioprine, an azathioprine metabolite, a nucleoside triphosphate inhibitor, mycophenolic acid, mycophenolate mofetil, 6-mercaptopurine, cyclophosphamide, mycophenolate, prednisolone, sirolimus, dexamethasone, rapamycin, FK506, mizoribine and tacrolimus.

18. The method of claim 15, wherein the ratio for Cu is 1/10, the ratio for L-thyroxine is 1/10, and the ratio for Au is 1/100.

19. The method of claim 15, wherein the measuring step is performed using inductively coupled plasma mass spectrometry or inductively coupled plasma optical emission spectrometry.

20. The method of claim 15, wherein the ratio for Cu is 1/5, the ratio for L-thyroxine is 1/5, and the ratio for Au is 1/50.

* * * * *

SEQUENCE LISTING

```
<160> NUMBER OF SEQ ID NOS: 1

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
```

-continued

```
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu
```